US010533201B2

United States Patent
Navickas et al.

(10) Patent No.: US 10,533,201 B2
(45) Date of Patent: Jan. 14, 2020

(54) ENZYMATIC TRANSPHOSPHORYLATION OF SUGAR SUBSTRATES

(71) Applicant: BASF SE, Ludwigshafen (DE)

(72) Inventors: Vaidotas Navickas, Mannheim (DE); Kai-Uwe Baldenius, Mannheim (DE); Michael Breuer, Darmstadt (DE); Patricia Wildberger, Wiener Neudorf (AT); Martin Pfeiffer, Graz (AT); Bernd Nidetzky, Graz (AT)

(73) Assignee: BASF SE, Ludwigshafen am Rhein (DE)

( * ) Notice: Subject to any disclaimer, the term of this patent is extended or adjusted under 35 U.S.C. 154(b) by 231 days.

(21) Appl. No.: 15/509,993

(22) PCT Filed: Jun. 30, 2015

(86) PCT No.: PCT/EP2015/064785
§ 371 (c)(1),
(2) Date: Mar. 9, 2017

(87) PCT Pub. No.: WO2016/037720
PCT Pub. Date: Mar. 17, 2016

(65) Prior Publication Data
US 2018/0148753 A1 May 31, 2018

(30) Foreign Application Priority Data

Sep. 10, 2014 (EP) .................................... 14184303

(51) Int. Cl.
| | | |
|---|---|---|
| *C07H 11/04* | (2006.01) | |
| *C12P 19/02* | (2006.01) | |
| *C12P 19/26* | (2006.01) | |
| *C12N 9/10* | (2006.01) | |
| *C12N 9/16* | (2006.01) | |
| *C07H 1/02* | (2006.01) | |

(52) U.S. Cl.
CPC ................ *C12P 19/02* (2013.01); *C07H 1/02* (2013.01); *C07H 11/04* (2013.01); *C12N 9/1051* (2013.01); *C12N 9/16* (2013.01); *C12P 19/26* (2013.01); *C12Y 204/01* (2013.01); *C12Y 204/01007* (2013.01); *C12Y 301/0301* (2013.01)

(58) Field of Classification Search
CPC ........... C07H 11/04; C07H 1/02; C12P 19/02; C12Y 204/01; C12Y 204/02007; C12Y 301/0301
See application file for complete search history.

(56) References Cited

U.S. PATENT DOCUMENTS

2013/0012475 A1  1/2013 Auriol et al.

FOREIGN PATENT DOCUMENTS

| EP | 2150620 A2 | 2/2010 |
|---|---|---|
| WO | WO-2005073399 A1 | 8/2005 |
| WO | WO-2008142155 A2 | 11/2008 |
| WO | WO-2009004093 A1 | 1/2009 |

OTHER PUBLICATIONS

Cottrill, M., et al., "Inositol phosphatase activity of the *Escherichia coli* agp-encoded acid glucose-1-phosphatase", Canadian Journal of Microbiology, vol. 48, No. 9, (2002), pp. 801-809.
Herter, T., et al., "Glucose-1-phosphatase (AgpE) from *Enterobacter cloacae* displays enhanced phytase activity", Applied Microbiology and Biotechnology, vol. 70, No. 1, (2006), pp. 60-64.
International Search Report for PCT/EP2015/064785 dated Oct. 21, 2015.
Pradel, E., et al., "Acid Phosphatases of *Escherichia coli:* Molecular Cloning and Analysis of agp, the Structural Gene for a Periplasmic Acid Glucose Phosphatase", Journal of Bacteriology, vol. 170, No. 10, (1988), pp. 4916-4923.
Saier, M. Jr., et al., "Sugar Phosphate: Sugar Transphosphorylation and Exchange Group Translocation Catalyzed by the Enzyme II Complexes of the Bacterial Phosphoenolpyruvate: Sugar Phosphotransferase System", The Journal of Biological Chemistry, vol. 252, No. 24, (1977), pp. 8899-8907.
Written Opinion of the International Searching Authority for PCT/EP2015/064785 dated Oct. 21, 2015.

*Primary Examiner* — Karen Cochrane Carlson
(74) *Attorney, Agent, or Firm* — Drinker Biddle & Reath LLP

(57) ABSTRACT

The present invention relates to methods of producing sugar phosphates by enzymatic transphosphorylation, wherein the phosphoryl transfer from phosphate donor substrates to sugar substrates is catalyzed by an enzyme having alpha-glucose-1-phosphatase activity. Furthermore, the present invention relates to a biocatalyst having sucrose phosphorylase as well as alpha-glucose-1-phosphatase activity and its use. The production of an enzyme having alpha-glucose-1-phosphatase activity and its use in the transphosphorylation of sugar substrates is also presented herein.

9 Claims, 10 Drawing Sheets

Specification includes a Sequence Listing.

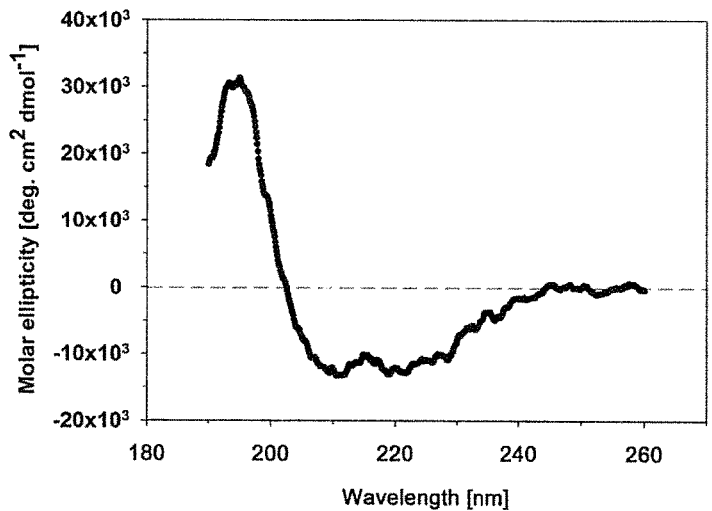

Figure 3

```
  1 MASWSHPQFE KIEGRQTVPE GYQLQQVLMM SRHNLRAPLA NNGSVLEQST
 51 PNKWPEWDVP GGQLTTKGGV LEVYMGHYMR EWLAEQGMVK SGECPPPDTV
101 YAYANSLQRT VATAQFFITG AFPGCDIPVH HQEKMGTMDP TFNPVITDDS
151 AAFSEKAVAA MEKELSKLQL TDSYQLLEKI VNYKDSPACK EKQQCSLVDG
201 KNTFSAKYQQ EPGVSGPLKV GNSLVDAFTL QYYEGFPMDQ VAWGEIKSDQ
251 QWKVLSKLKN GYQDSLFTSP EVARNVAKPL VSYIDKALVT DRTSAPKITV
301 LVGHDSNIAS LLTALDFKPY QLHDQNERTP IGGKIVFQRW HDSKANRDLM
351 KIEYVYQSAE QLRNADALTL QAPAQRVTLE LSGCPIDANG FCPMDKFDSV
401 LNEAVK
```

Figure 4

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of artificial sequence: synthetic primer

<400> SEQUENCE: 1
atgaacaaaa cgctaatcac c              21

<210> SEQ ID NO 2
<211> LENGTH: 22
<212> TYPE: DNA
<213> ORGANISM: Artificial Sequence
<220> FEATURE:
<223> OTHER INFORMATION: Description of artificial sequence: synthetic primer

<400> SEQUENCE: 2
ttatttcacc gcttcattca ac             22

<210> SEQ ID NO 3
<211> LENGTH: 70
<212> TYPE: DNA
<213> ORGANISM: Artificial Sequence
<220> FEATURE:
<223> OTHER INFORMATION: Description of artificial sequence: synthetic primer

<400> SEQUENCE: 3
atggctagct ggagccaccc gcagttcgaa aaaatcgaag ggcgccaaac cgtaccggaa     60
ggctatcagc                                                            70

<210> SEQ ID NO 4
<211> LENGTH: 43
<212> TYPE: DNA
<213> ORGANISM: Artificial Sequence
<220> FEATURE:
<223> OTHER INFORMATION: Description of artificial sequence: synthetic primer

<400> SEQUENCE: 4
catccgccaa aacagccaag cttattattt caccgcttca ttc      43

<210> SEQ ID NO 5
<211> LENGTH: 46
<212> TYPE: DNA
<213> ORGANISM: Artificial Sequence
<220> FEATURE:
<223> OTHER INFORMATION: Description of artificial sequence: synthetic primer

<400> SEQUENCE: 5
gtttaacttt aagaaggaga tatacatatg gctagctgga gccacc        46

<210> SEQ ID NO 6
<211> LENGTH: 21
<212> TYPE: PRT
<213> ORGANISM: Artificial Sequence
<220> FEATURE:
<223> OTHER INFORMATION: Description of artificial sequence: synthetic peptide

<400> SEQUENCE: 6

Lys Asp Ser Pro Ala Cys Lys Glu Lys Gln Gln Cys Ser Leu Val Asp
1               5                   10                  15

Gly Lys Asn Thr Phe
            20

<210> SEQ ID NO 7
<211> LENGTH: 406
<212> TYPE: PRT
<213> ORGANISM: Escherichia coli

<400> SEQUENCE: 7

Met Ala Ser Trp Ser His Pro Gln Phe Glu Lys Ile Glu Gly Arg Gln
1               5                   10                  15

Thr Val Pro Glu Gly Tyr Gln Leu Gln Gln Val Leu Met Met Ser Arg
            20                  25                  30

His Asn Leu Arg Ala Pro Leu Ala Asn Asn Gly Ser Val Leu Glu Gln
            35                  40                  45

Ser Thr Pro Asn Lys Trp Pro Glu Trp Asp Val Pro Gly Gly Gln Leu
50                  55                  60

Thr Thr Lys Gly Gly Val Leu Glu Val Tyr Met Gly His Tyr Met Arg
65                  70                  75                  80

Glu Trp Leu Ala Glu Gln Gly Met Val Lys Ser Gly Glu Cys Pro Pro
                85                  90                  95

Pro Asp Thr Val Tyr Ala Tyr Ala Asn Ser Leu Gln Arg Thr Val Ala
            100                 105                 110

Thr Ala Gln Phe Phe Ile Thr Gly Ala Phe Pro Gly Cys Asp Ile Pro
            115                 120                 125

Val His His Gln Glu Lys Met Gly Thr Met Asp Pro Thr Phe Asn Pro
            130                 135                 140

Val Ile Thr Asp Asp Ser Ala Ala Phe Ser Glu Lys Ala Val Ala Ala
145                 150                 155                 160

Met Glu Lys Glu Leu Ser Lys Leu Gln Leu Thr Asp Ser Tyr Gln Leu
                165                 170                 175

Leu Glu Lys Ile Val Asn Tyr Lys Asp Ser Pro Ala Cys Lys Glu Lys
            180                 185                 190

Gln Gln Cys Ser Leu Val Asp Gly Lys Asn Thr Phe Ser Ala Lys Tyr
            195                 200                 205

Gln Gln Glu Pro Gly Val Ser Gly Pro Leu Lys Val Gly Asn Ser Leu
            210                 215                 220

Val Asp Ala Phe Thr Leu Gln Tyr Tyr Glu Gly Phe Pro Met Asp Gln
225                 230                 235                 240

Val Ala Trp Gly Glu Ile Lys Ser Asp Gln Gln Trp Lys Val Leu Ser
                245                 250                 255

Lys Leu Lys Asn Gly Tyr Gln Asp Ser Leu Phe Thr Ser Pro Glu Val
            260                 265                 270

Ala Arg Asn Val Ala Lys Pro Leu Val Ser Tyr Ile Asp Lys Ala Leu
            275                 280                 285

Val Thr Asp Arg Thr Ser Ala Pro Lys Ile Thr Val Leu Val Gly His
            290                 295                 300

Asp Ser Asn Ile Ala Ser Leu Leu Thr Ala Leu Asp Phe Lys Pro Tyr
305                 310                 315                 320

Gln Leu His Asp Gln Asn Glu Arg Thr Pro Ile Gly Gly Lys Ile Val
                325                 330                 335

Phe Gln Arg Trp His Asp Ser Lys Ala Asn Arg Asp Leu Met Lys Ile

-continued

```
                340                 345                 350
Glu Tyr Val Tyr Gln Ser Ala Glu Gln Leu Arg Asn Ala Asp Ala Leu
        355                 360                 365

Thr Leu Gln Ala Pro Ala Gln Arg Val Thr Leu Glu Leu Ser Gly Cys
        370                 375                 380

Pro Ile Asp Ala Asn Gly Phe Cys Pro Met Asp Lys Phe Asp Ser Val
385                 390                 395                 400

Leu Asn Glu Ala Val Lys
                405
```

ENZYMATIC TRANSPHOSPHORYLATION OF SUGAR SUBSTRATES

CROSS-REFERENCE TO RELATED APPLICATIONS

This application is a national stage application (under 35 U.S.C. § 371) of PCT/EP2015/064785, filed Jun. 30, 2015, which claims benefit of European Application No. 14184303.7, filed Sep. 10, 2014, both of which are incorporated herein by reference in their entirety.

The present invention relates to methods of producing sugar phosphates by enzymatic transphosphorylation, wherein the phosphoryl transfer from phosphate donor substrates to sugar substrates is catalyzed by an enzyme having alpha-glucose-1-phosphatase activity. In another aspect, the present invention relates to a biocatalyst having sucrose phosphorylase as well as alpha-glucose-1-phosphatase activity and its use. According to a further aspect, the present invention also relates to the production of an enzyme having alpha-glucose-1-phosphatase activity and its use in the transphosphorylation of sugar substrates.

Phosphorylation of sugar substrates is a common biochemical transformation of central importance to cellular metabolism (1-3). It usually involves phosphoryl transfer from a phospho-activated donor substrate such as ATP to an acceptor group, typically a hydroxyl, on the sugar backbone (4-7). Various phosphotransferases catalyze sugar phosphorylation (8-12). In an alternative reaction catalyzed by glycoside phosphorylases, where phosphorylation occurs exclusively at the sugar's anomeric position, a glycosyl residue is transferred from a sugar donor substrate to phosphate (FIG. 1A) (13-14). The phosphomonoester moiety attached to sugars is a key element of biological recognition, across all steps of glycolysis for example, and it serves to prime sugars for further conversion in different biochemical pathways (15-18). It is known from intracellular metabolite profiling studies that concentration changes of common sugar phosphates (e.g. D-glucose-6-phosphate, Glc-6-P; D-fructose-6-phosphate, Fru-6-P) are often linked to major alterations in cellular physiology (19-22). Due to the requirement of authentic reference material in different biological investigations, there is considerable interest in the synthetic preparation of sugar phosphates (20). Technologically, sugar phosphates are applied as nutritional supplements and taste enhancers in food and feed products; moisturizing ingredients in cosmetics; ionic surface-active reagents in detergents; and building blocks of new polymers (23-25).

Naturally known phosphorylation reactions have been exploited with mixed success for the biocatalytic synthesis of sugar phosphates. Glycosyl transfer to phosphate is fundamentally limited in application to hexose-1-phosphate products, and the relatively narrow substrate scope of glycoside phosphorylase reactions restricts one to just a few glycosyl phosphates for which effective production has been demonstrated at preparative scale (e.g. alpha- and beta-Glc-1-P (26, 27), alpha-D-galactose 1-phosphate (28)). Phosphotransferase reactions by contrast offer convenient access to a large diversity of sugar phosphate products, as shown for nucleoside triphosphate dependent phosphorylation of various hexose substrates by sugar kinases for example (29-33). However, high costs of the phospho-activated donor substrate and enzyme inhibition by the resulting dephosphorylation product (e.g. ADP from ATP) necessitate that the phosphoryl donor is supplied in only catalytic amounts and therefore regenerated continuously during the reaction (FIG. 1B) (34, 35). This makes the biocatalytic phosphoryl transfer a technically complex overall transformation of currently limited use in sugar phosphate synthesis.

Transphosphorylation catalyzed by phosphatases in an alteration of their natural phosphomonoester hydrolysis reaction has been considered as alternative route towards sugar phosphates (FIG. 1C) (36-39). Under conditions where sugar was present in a concentration high enough to effectively outcompete the reaction with water, some phosphatases (e.g. acid phosphatase) promoted sugar phosphate formation in moderate (e.g. D-mannose 6-phosphate; 15%) to excellent yields (e.g. Glc-6-P; up to 95%) (37). Usage of expedient phosphoryl donor substrates such as inorganic pyro- or oligo-phosphate was advantageous. However, high preponderance of donor substrate hydrolysis, fast secondary hydrolysis of sugar phosphate product, and combined inhibition and mass action effects of the released phosphates (FIG. 1C) are critical issues of phosphatase-catalyzed synthesis (40, 41). Transphosphorylation systems with improved synthetic efficacy therefore still need to be identified.

It was an objective of the present invention to provide a system for the efficient production of sugar phosphates in good yields. In particular, it was an objective of the present invention to provide methods and materials for enzymatic phosphoryl transfer from various phosphate donor substrates to sugar substrates.

The inventors of the present invention were able to demonstrate, that an enzyme having alpha-glucose-1-phosphatase activity is able to efficiently catalyze transphosphorylation reactions between a large variety of phosphate donors and sugar substrates and is therefore a highly powerful tool for a flexible production of sugar phosphates.

An objective of the present invention as set out above is therefore met by a method of producing one or more sugar phosphates by enzymatic transphosphorylation comprising the following steps:

(i) providing one or more sugar substrates,
(ii) providing one or more phosphate donor substrates,
(iii) providing an alpha-glucose-1-phosphatase or an enzyme having alpha-glucose-1-phosphatase activity,
(iv) incubating the one or more sugar substrates provided in step (i) and the one or more phosphate donor substrates provided in step (ii) with the alpha-glucose-1-phosphatase or, respectively, the enzyme having alpha-glucose-1-phosphatase activity provided in step (iii) under conditions which allow transphosphorylation,
(v) optionally, purifying one or more sugar phosphates obtained in step (iv).

In the context of the present invention the term transphosphorylation refers to the transfer of one or more phosphate group(s) from a donor substrate to an acceptor substrate.

A substrate in the context of the present invention, may be any molecule capable of donating or accepting one or more phosphate group(s), in one or more positions. In particular, substrates in the context of the present invention are phosphorylated or unphosphorylated carbohydrates, for example aldoses or ketoses.

The enzyme provided in step (iii) of the above detailed method may be any catalytic entity consisting of one or more enzymes or fragments thereof, which is able to catalyze alpha-glucose-1-phosphate hydrolysis (for example an enzyme of enzyme class EC3.1.3.10 (glucose-1-phosphatase)). In particular, the enzyme provided may be an alpha-glucose-1-phosphatase. For example, the agp gene product, α-Glc-1-P phosphatase, from *Escherichia coli* may be used.

With respect to the conditions which allow transphosphorylation to be adjusted in step (iv), it has already been mentioned above that the concentration of the sugar substrate has to outcompete effectively the reaction with water in order to promote sugar phosphate formation in a high yield.

In the context of the present invention it has been found out, that when an 5 to 30-fold excess of sugar substrate is added to conversions of sugar phosphates by a sugar phosphatase, surprisingly the conversion rate may increase up to about 5-fold in hyperbolic dependence of the sugar substrate concentration. The phosphate release rate was decreased at the same time compared to the control reaction performed in the absence of sugar substrate. Surprisingly, the phosphatase was somehow "activated" in the presence of external acceptor. Furthermore, in spite of the pronounced hydrolase activity of the phosphatase towards each sugar phosphate synthesized in the reaction, advantageously no loss of transphosphorylation product to secondary hydrolysis was observed in the timespan of the experiment. Unlike other phosphatase-catalyzed transphosphorylation reactions in which product kinetic stability presented a problem to synthetic application of the biocatalytic transformations (37, 38), sugar phosphates were formed as if they were real equilibrium products, thus enabling their convenient production.

Many phosphatases of the histidine acid phosphatase family exhibit their optimum activity in the acidic pH range (≤5.0). As shown in the context of the present invention, however, the activity is constant in the pH range 4.0-6.0 and only gradually decreases at higher pH.

In a preferred embodiment of the above described method, the sugar substrate(s) is/are selected from the group consisting of aldoses and ketoses, preferably from the group consisting of glucose, glucosamine, N-acetyl glucosamine, fructose, galactose, fucose, mannose, sorbose, xylose, arabinose, xylitol, arabitol, rhamnose and N-acetyl neuraminic acid and the phosphates of these sugars, preferably the mono-phosphates of these sugars.

According to a further preferred embodiment of the above described method, the one or more phosphate donor substrate(s) is/are selected from the group consisting of alpha-glucose-1-phosphate, glucose-6-phosphate, fructose-6-phosphate and fructose-1-phosphate.

It has been demonstrated in the context of the present invention, that various sugar substrates may be efficiently phosphorylated by the method described herein using a range of phosphate donor substrates, advantageously providing flexible production of desired sugar phosphates.

In a particularly preferred embodiment of the method according to the invention, the phosphate donor substrate or one of the phosphate donor substrates provided in step (ii) is alpha-glucose-1-phosphate.

The Cori ester alpha-glucose-1-phosphate (α-Glc 1-P) is a central intermediate of cellular carbohydrate metabolism. Its free energy of hydrolysis ($\Delta G°\_hydrolysis$) at 25° C. is −5.0 kcal/mol, which is similar to pyrophosphate ($\Delta G°\_hydrolysis$=−4.6 kcal/mol) and places α-Glc 1-P only slightly below ATP ($\Delta G°\_hydrolysis$=−7.3 kcal/mol) in terms of energy content (2). α-Glc 1-P is produced conveniently from different saccharides, especially from sucrose (26). Its glycosidic phosphomonoester group primes α-Glc 1-P for flexible exploitation in glucosyl and phosphoryl transfer reactions, however up to now, biocatalytic use of α-Glc 1-P was restricted entirely to glucoside synthesis (e.g. (42, 43)).

According to a further preferred embodiment, in the method of the present invention, the step (ii) comprises an enzymatic conversion of sucrose to D-fructose and alpha-D-glucose-1-phosphate by a sucrose phosphorylase [EC 2.4.1.7] or an enzyme having sucrose phosphorylase activity in the presence of phosphate or one or more sources of phosphate.

Conveniently, the alpha-D-glucose-1-phosphate as the or one of the phosphate donor substrate(s) may be provided by simple conversion of sucrose to D-fructose and alpha-D-glucose-1-phosphate by a sucrose phosphorylase or an enzyme having sucrose phosphorylase activity in the presence of phosphate. This allows to use sucrose as an inexpensive educt by a simple enzymatic conversion.

In a particularly preferred embodiment of the method described above, step (ii) and step (iv) and, optionally, step (iii), are carried out simultaneously, preferably in a one-pot-reaction.

Advantageously, conversion of sucrose to D-fructose and alpha-D-glucose-1-phosphate by a sucrose phosphorylase or an enzyme having sucrose phosphorylase activity in the presence of phosphate as well as the transphosphorylation reaction may conveniently be performed in a one-pot-reaction without a need for an intervening separation or purification step.

In a further aspect the present invention provides a biocatalyst having sucrose phosphorylase activity and alpha-glucose-1-phosphatase activity and/or comprising or consisting of a sucrose phosphorylase and an alpha-glucose-1-phosphatase.

A further aspect of the present invention therefore pertains to the use of the above mentioned biocatalyst in a method as described herein before.

In the context of the present invention the term biocatalyst refers to any catalytic entity having the specified activity or activities and may be a single bi- or multifunctional enzyme as well as a mixture of two or more enzymes or fragments thereof.

The biocatalyst according to the present invention provides a single product ready to use for performing steps (ii) and (iv) of the above described method in a one-pot reaction, without a need for adjustment of reaction conditions. Thus, it allows sugar phosphate production in a single reaction set-up resulting in high yields of the desired sugar phosphate product(s).

In a further preferred embodiment of the method of the present invention, step (iii) comprises the expression of an alpha-glucose-1-phosphatase or an enzyme having alpha-glucose-1-phosphatase activity by a host cell, preferably in the cytoplasm of a host cell.

A large range of microorganisms known to be suitable for biotechnologic applications may be used as host cell for homologous or heterologous expression of the desired enzyme.

Step (iii) may for example comprise the expression of a nucleotide sequence having a nucleotide sequence identity to the agp gene of *E. coli* of more than 75%, preferably more than 85%, more preferably more than 95%, most preferably more than 99%, in a host cell, preferably in the cytoplasm of a host cell.

In the context of the present invention, nucleotide sequence similarities are determined with the aid of the Waterman-Smith algorithm with a gap open penalty of 10, a gap extension penalty of 0.5 and the Blosum62 matrix. The Waterman-Smith algorithm is described in Smith, T. F. and Waterman, M. S., "Identification of common molecular subsequences", Journal of Molecular Biology (1981), 147: 195 to 197 and, for example, implemented on-line by means of the corresponding tool page of the EMBL, currently "EMBOSS:water" obtainable via www.ebi.ac.uk/tools/emboss/align/.

Furthermore, in a preferred embodiment, the alpha-glucose-1-phosphatase or the enzyme having alpha-glucose-1-phosphatase activity, respectively, is expressed as a recombinant fusion protein comprising a tag suitable for isolation of the alpha-glucose-1-phosphatase or the enzyme having alpha-glucose-1-phosphatase activity.

For example, the E. coli alpha-glucose-1-phosphatase which is derived by expression of the agp gene has been demonstrated in the context of the present invention to be a powerful biocatalyst for the above described transphosphorylation reactions.

In a further aspect the present invention therefore relates to the use of an alpha-glucose-1-phosphatase or of an enzyme having alpha-glucose-1-phosphatase activity for the transphosphorylation of one or more sugar substrates, in particular aldoses and ketoses.

Alpha-glucose-1-phosphatase is the first biocatalyst reported in the context of the present invention for successful use in transphosphorylation reactions for flexible production of various sugar phosphates.

A further aspect of the present invention relates to a method for the production of a recombinant fusion protein having an amino acid sequence identity to the alpha-glucose-1-phosphatase of E. coli of more than 75%, preferably more than 85%, more preferably more than 95%, most preferably more than 99%, and having a tag suitable for isolation of the protein, comprising the step of expressing the nucleotide sequence in a host cell, preferably in the cytoplasm of a host cell.

Amino acid sequence similarities are in the context of the present invention also determined with the aid of the Waterman-Smith algorithm with a gap open penalty of 10, a gap extension penalty of 0.5 and the Blosum62 matrix as mentioned above.

Expression of an enzyme as a fusion protein having a tag suitable far isolation of the protein, such as for example a Strep-tag, allows easy and efficient purification of the enzyme using standard protocols.

Overexpression of the agp gene in E. coli results in accumulation of recombinant enzyme in the periplasmic space whereby the 22 amino acid-long N-terminal targeting sequence is processed off correctly (59, 60). Nevertheless, cytoplasmic production of α-Glc 1-P phosphatase would be useful because the absence of N-terminal processing in the cytoplasm offers flexibility in modifying the N-terminus with a functional tag. When expressing the recombinant α-Glc 1-P phosphatase in the E. coli cytoplasm, however, the presence of disulfide bonds in the protein structure presents critical conjuncture for protein production under these conditions, which may be avoided if the endogenous disulfide bond isomerase (DsbC) is co-overexpressed (61). The final α-Glc 1-P phosphatase construct has the targeting sequence deleted and an N-terminal Strep-tag added for facilitated recovery.

Therefore, in a preferred embodiment of the above described method, an enzyme having disulfide bond isomerase activity is co-expressed with the recombinant fusion protein.

In yet a further aspect the present invention relates to a recombinant fusion protein having an amino acid sequence identity to the alpha-glucose-1-phosphatase of E. coli of more than 75%, preferably more than 85%, more preferably more than 95%, most preferably more than 99%, and having a tag suitable for isolation of the protein, preferably obtained or obtainable by a method as described above.

The recombinant fusion protein as specified above provides a powerful tool for the efficient production of a variety of sugar phosphates by enzymatic transphosphorylation.

The following examples and figures are added to illustrate the present invention without limiting the scope of protection.

DESCRIPTION OF THE FIGURES

FIG. 3: CD spectrum of αGlc 1-P phosphatase averaged from ten individual wavelength scans.

FIG. 4: Sequence coverage obtained by LC-MS/MS analysis of tryptic and chymotryptic peptides generated from purified αGlc 1-P phosphatase (SEQ ID NO 7). Matched peptides are bold.

CHEMICALS AND REAGENTS

Figure 1:
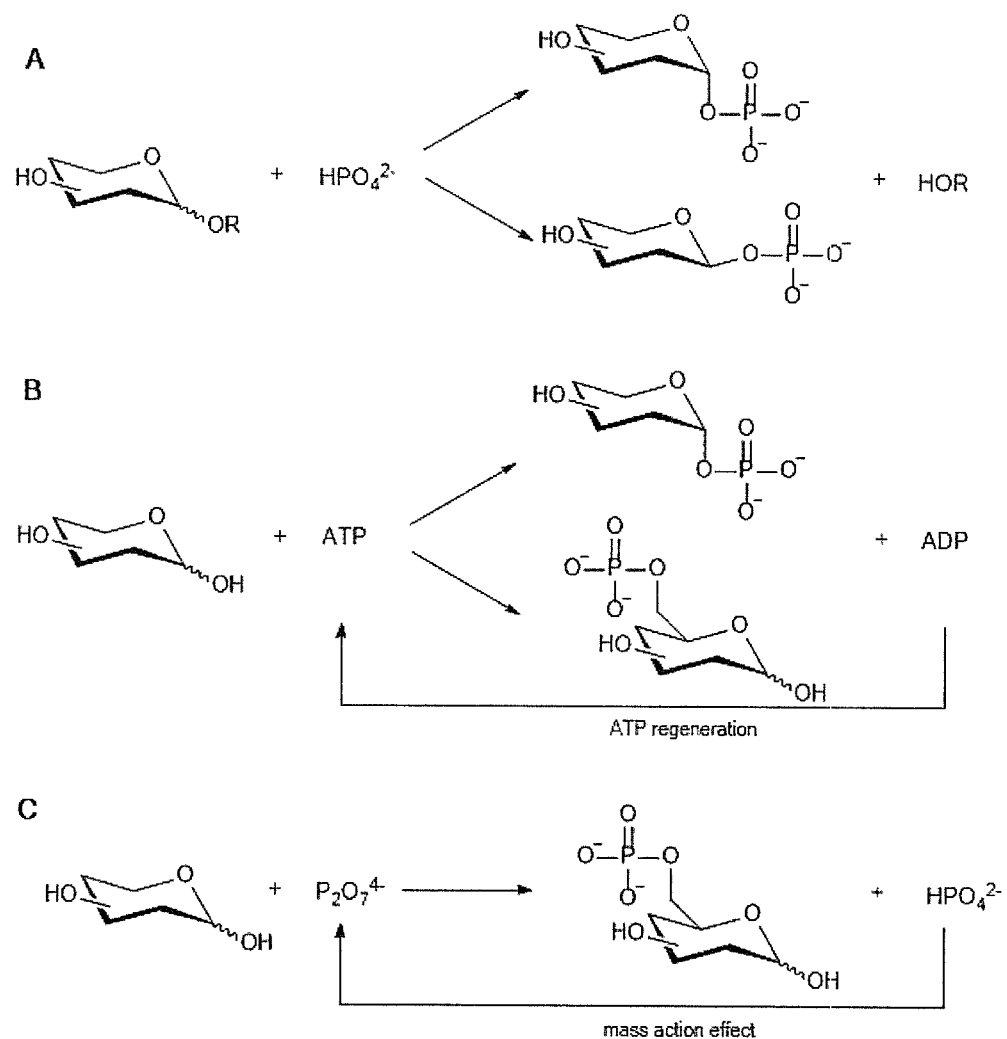
FIG. 1: Reactions catalyzed by disaccharide phosphorylases (A), kinases (B) and phosphatases (C).

Unless stated, all chemicals were of highest purity from Sigma-Aldrich (Vienna, Austria) or Roth (Karlsruhe, Germany). GeneJET genomic DNA purification kit was from Thermo Fisher Scientific (Waltham, USA). Oligonucleotides were from Sigma-Aldrich. DNA sequencing was performed at LGC Genomics (Berlin, Germany). Electrocompetent *E. coli* Origami B (DE3) cells were from Novagen (Merck KgaA, Darmstadt, Germany). $H_2^{18}O$ (97% isotopic purity) was from Sigma-Aldrich. The sodium salts of α-Glc 1-P, Glc 6-P, Fru 6-P, and pyrophosphate were from Sigma-Aldrich. The barium salt of Fru 1-P was also from Sigma-Aldrich. Phytate (sodium salt) was from Roth. The potassium salt of β-Glc 1-P (27) was from Prof. Tom Desmet (Ghent University, Belgium). N,O-bis(trimethylsilyl)trifluoroacetamide with 1% trimethylchlorosilane (BSTFA/1% TMCS) and pyridine were from Sigma-Aldrich. Purified preparations of sucrose phosphorylase from *Leuconostoc mesenteroides* (SPase) (51) and mannitol 1-phosphate dehydrogenase from *Aspergillus fumigatus* (52) were obtained by reported procedures.

Example 1: Enzyme Preparation and Characterization

α-Glc 1-P phosphatase is the agp gene product, and the enzyme is located to the *E. coli* periplasm (44). Crystal structure of the enzyme complex with glucosyl phosphate ligand reveals a two-domain protein topology typical of members of the high-molecular-weight histidine acid phosphatase family (45). The protein fold comprises a discrete α-helical domain next to a a/13 domain and a catalytic center located in a deep cleft between the two domains (45). The α-Glc 1-P phosphatase structure exhibits 3 disulfide bridges between $Cys^{94}$ and $Cys^{125}$, $Cys^{189}$ and $Cys^{195}$, as well as $Cys^{384}$ and $Cys^{392}$ (45). The active site contains a highly conserved histidine ($His^{18}$) that is thought to function as catalytic nucleophile. $Asp^{290}$ is the likely general acid-base catalyst, and the phosphomonoester group of α-Glc 1-P is held tightly in place through a cluster of positively charged residues ($Arg^{17}$, $Arg^{21}$, $Arg^{94}$, $His^{289}$) (45). The proposed catalytic reaction of α-Glc 1-P phosphatase follows a double displacement-like mechanism via a covalent phospho-histidine intermediate, as shown in FIG. 2A.

Molecular Cloning, Expression and Purification of αGlc 1-P Phosphatase.

*E. coli* BL21-Gold (DE3) cells were grown overnight at 30° C. in Lennox-medium. The cells were centrifuged at 20,000 g and 4° C. for 30 min. Pellet was used for preparation of genomic DNA. The gene encoding αGlc 1-P phosphatase was amplified by a PCR that used Phusion DNA polymerase (Thermo Fisher Scientific, Waltham, USA) in combination with oligonucleotide primers 1 (SEQ ID NO 1) and 2 (SEQ ID NO 2) (Table 1). PCR consisted of a pre-heating step at 98° C. for 5 min, followed by 30 reaction cycles of denaturation at 98° C. for 30 s, annealing at 70° C. for 30 s, and elongation at 72° C. for 1.5 min. The final extension step was carried out at 72° C. for 5 min. The presence of an N-terminal, 66 bp long signal sequence was predicted using SignalIP-4.1 at the Center of Biological Sequence Analysis (www.cbs.dtu.dk/services/SignalP-4.1/). To remove the N-terminal signal sequence, to add an N-terminal Strep-tag, and to also extend the gene end with overlapping regions to the vector, a PCR was performed in which oligonucleotide primers 3 (SEQ ID NO 3) and 4 (SEQ ID NO 4) were used (Table 1). To extend the gene start with overlapping regions to the vector, a PCR with primers 5 (SEQ ID NO 5) and 3 (SEQ ID NO 3) was performed. The final amplification product was treated by DpnI to digest the parental template. The final construct was cloned into the linearized pMS470_dsbC vector via Gibson assembly. Sequenced plasmid vectors harboring the structural gene were transformed into *E. coli* Origami B cells.

Recipient *E. coli* strains were cultivated in 1-L baffled shake flasks at 37° C. and 110 rpm using Lennox-medium containing 0.115 mg/mL ampicillin. When $OD_{600}$ had reached 0.8, temperature was decreased to 18° C. prior to induction with isopropyl-β-D-thiogalactopyranoside (0.01 mM). After 20 h, cells were centrifuged at 4° C. and 4,420 g for 30 min (Sorvall RC-5B Refrigerated Superspeed centrifuge; Du Pont Instruments, Newtown, USA). The pellet was resuspended in 50 mM Mes, pH 7.0, pH 7.0, and frozen at −20° C. Thawed cell suspension was passed twice through a French pressure cell press (American Instruments, Silver Springs, USA) at 150 bar, and cell debris was removed by centrifugation at 4° C., 20,000 g for 30 min.

αGlc 1-P phosphatase was isolated from the crude extract using a Strep-Tactin Sepharose column (IBA, Gottingen, Germany), using a general protocol described elsewhere (51). Pooled fractions containing αGlc 1-P phosphatase were loaded on a Fracto-gel EMD-DEAE column (Merck, Darmstadt, Germany) and purified according to standard protocol. Buffer exchange to 50 mM Mes, pH 7.0 (αGlc 1-P phosphatase) was performed using Amicon Ultra-15 Centrifugal Filter Units (Millipore, Billerica, USA). Note: Unless mentioned, all further experiments were done in 50 mM Mes buffer, pH 7.0. Purification was monitored by SDS-PAGE; protein bands were visualized by silver staining.

TABLE 1

Oligonucleotide primers used for molecular cloning of αGlc 1-P phosphatase.

| Primer | Sequence (5' → 3') |
|---|---|
| Primer 1 | ATGAACAAAACGCTAATCACC (SEQ ID NO 1) |
| Primer 2 | TTATTTCACCGCTTCATTCAAC (SEQ ID NO 2) |
| Primer 3 | ATGGCTAGCTGGAGCCACCCGCAGTTCGAAAAAATC GAAGGGCGCCAAACCGTACCGGAAGGCTATCAGC (SEQ ID NO 3) |
| Primer 4 | CATCCGCCAAAACAGCCAAGCTTATTATTTCACCGC TTCATTC (SEQ ID NO 4) |
| Primer 5 | GTTTAACTTTAAGAAGGAGATATACATATGGCTAGC TGGAGCCACC (SEQ ID NO 5) |

CD Spectroscopy.

Far-UV CD spectra of αGlc 1-P phosphatase (0.4 mg/mL) were recorded at 25° C. on a Jasco J715 spectro-polarimeter (JASCO Inst., Gross-Umstadt, Germany). CD spectra were collected in the wavelength range 190-260 nm at a scan speed of 100 nm/min using a bandwidth of 2.0 nm and a response time of 1.0 s. All spectra were recorded in a 0.01 cm cuvette. For each sample, 10 spectra were recorded, averaged, and buffer signal subtracted. CD spectra were evaluated by using Dichroweb (54) with reference database No. 4.

A far-UV circular dichroism (CD) spectrum from solution of α-Glc 1-P phosphatase us shown in FIG. 3. Estimates of the relative content of secondary structural elements are summarized in Table 2 where they are compared to data derived from the experimental protein structures. The results agree in showing that α-helices were present in slight excess over β-strands and that a substantial portion of the structure was classified as unordered. There is no hint at major protein misfolding in the recombinant enzyme preparations used.

TABLE 2

Relative content of secondary structural elements in αGlc 1-P phosphatase obtained from the CD spectra and from the crystal structure (in parenthesis).

| Secondary structure | αGlc 1-P phosphatase [%] |
|---|---|
| Alpha helices | 51 (39) |
| Beta strands | 22 (14) |
| Turns | 11 (47) |
| Unordered | 16 |

Mass Spectrometry.

For sample preparation, purified αGlc 1-P phosphatase (5 μg) was incubated with 20 mM iodoacetamide (IAA) solution for 30 min at 37° C. and digested with modified trypsin (Promega, Madison, USA) (55), and/or with 0.5 μg chymotrypsin (Roche Applied Sciences, Penzberg, Germany) in 50 mM ammonium bicarbonate and 10 mM $CaCl_2$. For MS analysis, digests were acidified to 0.1% formic acid and separated by nano-HPLC (Dionex Ultimate 3000) equipped with a μ-precolumn (C18, 5 μm, 100 Å, 5×0.3 mm) and a Acclaim PepMap RSLC nanocolumn (C18, 2 μm, 100 Å, 150×0.075 mm) (all Thermo Fisher Scientific). About 0.5 μg of digested protein were injected and concentrated on the enrichment column for 2 min at a flow rate of 20 μL/min with 0.5% trifluoroacetic acid as isocratic solvent. Separation was carried out on the nanocolumn at a flow rate of 300 nL/min using the following gradient, where solvent A is 0.05% trifluoroacetic acid in water and solvent B is 0.05% trifluoroacetic acid in 80% acetonitrile: 0-2 min: 4% B; 2-70 min: 4-28% B; 70-94 min: 28-50% B, 94-96 min: 50-95% B; 96-116 min: 95% B; 116-116.1 min: 95-4% B; 116.1-140 min: re-equilibration at 4% B. The sample was ionized in the nanospray source equipped with stainless steel emitters (ES528, Thermo Fisher Scientific) and analyzed in a Orbitrap velos mass spectrometer (Thermo Fisher Scientific) operated in positive ion mode, applying alternating full scan MS (m/z 400 to 2000) in the ion cyclotron and MS/MS by higher-energy collisional dissociation of the 20 most intense peaks with dynamic exclusion enabled. The LC-MS/MS data were analyzed by searching a database containing the protein sequences of αGlc 1-P phosphatase and known background proteins with Mascot 2.3 (MatrixScience, London, UK). Search criteria were charge 2+ or 3+, precursor mass error 0.05 Da, and product mass error 0.7 Da, and carbamidomethylation, oxidation on methionine, −2H on cysteine (disulfide) as variable modifications. A maximum false discovery rate of 0.05 using decoy database search, an ion score cut off of 20 and a minimum of 2 identified peptides were chosen as protein identification criteria.

Liquid chromatography-tandem mass spectrometry was applied to the determination of disulfide bond(s) in the as-isolated preparation of recombinant α-Glc 1-P phosphatase. Protein digests with trypsin or chymotrypsin were resolved to 62% overall sequence coverage, 214 peptides, 37 unique peptides, and a Mascot score of 6046 (FIG. 4). Identity of one of the three native disulfide bonds between $Cys^{189}$ and $Cys^{195}$ was confirmed unambiguously from the peptide KDSPACKEKQQCSLVDGKNTF (SEQ ID NO 6) (ion score: 34; expect 0.00042). The results are clear in showing that disulfide bond formation was possible under the expression conditions used.

Assays.

Specific activity of α-Glc 1-P phosphatase was determined at 37° C. and pH 7.0 using 20 mM αGlc 1-P as substrate. Reaction was started by addition of α-Glc 1-P phosphatase (0.1 μM), and release of free phosphate was measured over 75 min. Inorganic phosphate was determined colorimetrically at 850 nm (56).

α-Glc 1-P and Glc 6-P were measured in a coupled enzymatic system with phosphoglucomutase and Glc 6-P dehydrogenase (57). Fru 6-P was measured using an assay with mannitol 1-phosphate dehydrogenase (52). Fru 1-P was measured indirectly from the phosphate mass balance for substrate consumed (Δ[αGlc 1-P]) and products formed (equation 1), or directly using HPAEC-PAD (see later).

$$\Delta[\alpha Glc\ 1\text{-}P] = [Fru\ 1\text{-}P] + [Glc\ 6\text{-}P] + [Fru\ 6\text{-}P] + [phosphate] \quad (1)$$

The total protein concentration was measured using Roti-Quant assay referenced against BSA (58).

Phosphatase Kinetics.

Hydrolysis reactions were carried out at an initial substrate concentration of 20 mM. The different substrates used are summarized in Table 3. Reactions were started by addition of enzyme (α-Glc 1-P phosphatase, 0.1 μM), and incubations continued for up to 150 min at 37° C. and a thermomixer agitation rate of 650 rpm. Samples were taken in 15 min intervals, heat-treated (99° C., 5 min), and centrifuged at 20,000 g for 5 min. The release of phosphate was measured, and the initial rate V (mM min$^{-1}$) was determined from the linear relationship between phosphate concentration and time. Apparent turnover frequencies ($k_{cat\_app}$; s$^{-1}$) were calculated with equation 2, where [E] is the molar enzyme concentration, determined from the protein concentration assuming a molecular mass of 45 kDa for αGlc 1-P phosphatase.

$$k_{cat\_app}=V/[E] \quad (2)$$

TABLE 3

Apparent turnover frequencies for hydrolysis of phosphorylated sugars. The S.D. for $k_{cat\_app}$ was equal to or smaller than 10% of the reported value, except 14%, 18%, and 24%.

| Substrate | αGlc 1-P phosphatase $k_{cat\_app}$ [s$^{-1}$] |
|---|---|
| αGlc 1-P | 40 |
| βGlc 1-P | n.d. |
| Glc 6-P | 56 |
| Fru 1-P | 22 |
| Fru 6-P | 22$^a$ |
| Phytate | 2.1 |
| Pyrophosphate | n.d. | n.d., no activity above assay detection limit.

Example 2: Mechanistic Studies

Inorganic Phosphate-Water Medium $^{18}$O Exchange During, Hydrolysis, of αGlc 1-P.

All reaction mixtures were prepared from H$_2$$^{18}$O (97%) to give a final $^{18}$O isotopic purity of the water solvent of 90%. Phosphatase reactions were done using 2.0 mM αGlc 1-P as the substrate. The standard Mes and Hepes buffers were used. Phosphorylase reaction was done in 50 mM Mes buffer, pH 7.0, using 1.0 mM αGlc 1-P. Reactions were started by adding enzyme (0.1 μM, sucrose phosphorylase: 14 μM) to substrate solution at 37° C. Incubations proceeded for 2 h using agitation at 650 rpm in an Eppendorf thermomixer. Reactions were stopped by heating (99° C., 5 min). Control reactions were carried out in exactly the same way using normal H$_2$$^{16}$O instead of H$_2$$^{18}$O. Conversion of αGlc 1-P substrate was 90% or higher in each sample.

Incorporation of $^{18}$O-label into phosphate was analyzed by GC-MS. Samples were dried in a SpeedVac for 3 h and derivatized with BSTFA/1% TMCS, in pyridine (1:2, by volume). Analysis was performed using a Trace DSQ Single Quadrupole GC-MS instrument (Thermo Scientific). The following GC parameters were used: injection volume, 1 μL; injector temperature, 250° C.; carrier gas, He; carrier gas flow, 1 mL/min; column, HP-5MS (60 m, ID 0.250 mm, film thickness 0.25 μm) from Agilent (Waldbronn, Germany). The temperature gradient was as follows: starting temperature, 110° C. for 4 min; ramp to 300° C. at a heating rate of 20° C./min; final hold time, 10 min. The MS was operated in EI mode (source temperature: 280° C.) and the detected mass range was 50-700 m/z. The extracted ion chromatograms of m/z 299 and m/z 301 were integrated using the Xcalibur 1.4 software (Thermo Scientific).

Mechanistic Characterization of α-Glc 1-P Hydrolysis Using $^{18}$O Labeling.

Figure 2:
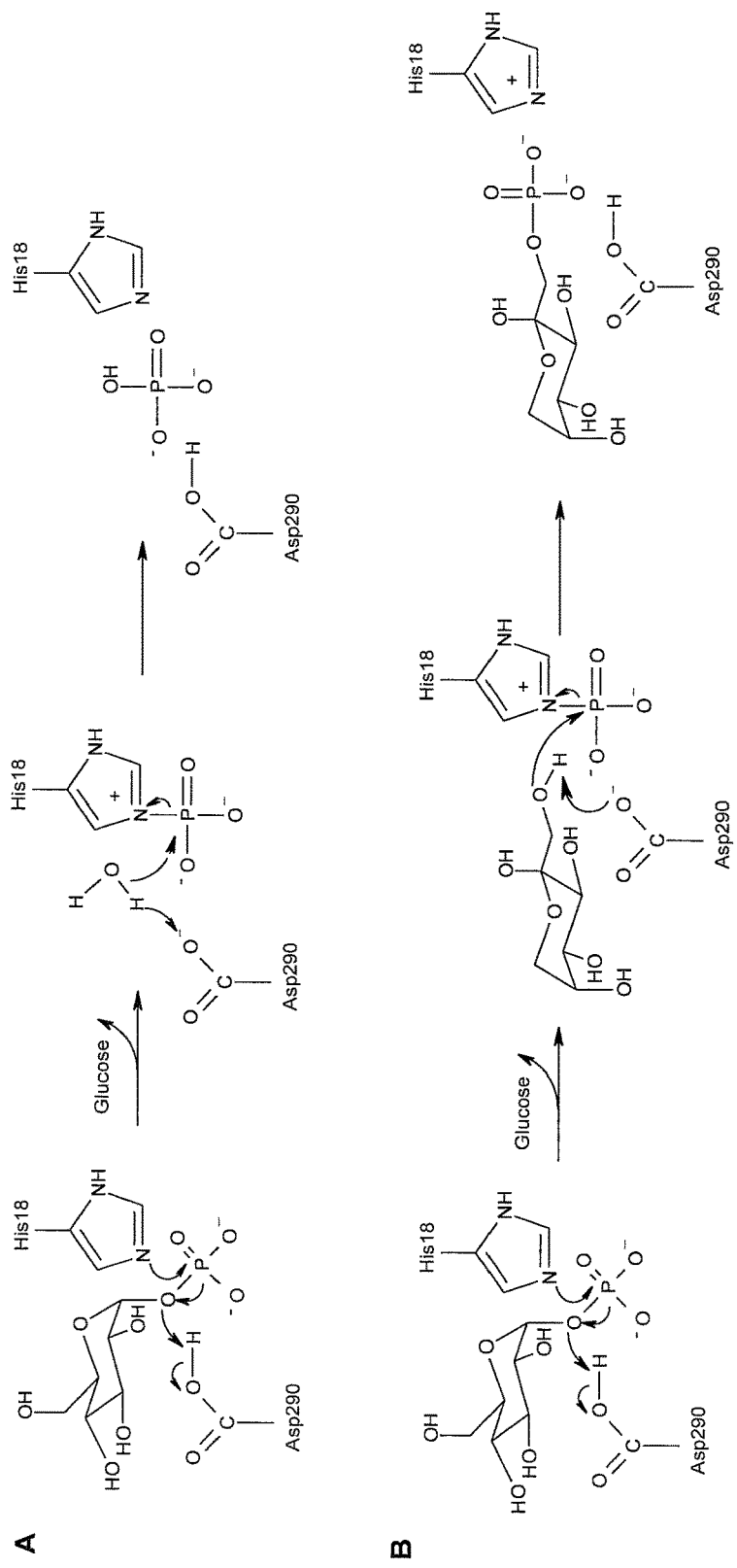
FIG. 2: Proposed double displacement-like mechanism of hydrolysis of αGlc 1-P catalyzed by αGlc 1-P phosphatase (A). (B) Phosphoryl group-transfer from αGlc 1-P to Fru catalyzed by αGlc 1-P phosphatase.

In the proposed catalytic reaction of α-Glc 1-P phosphatase the O1-P bond of substrate is cleaved, and that water (from solvent) attacks a phospho-enzyme intermediate in the dephosphorylation step of the overall hydrolytic conversion of α-Glc 1-P (FIG. 2). Contrary to uncatalyzed and glycosidase-like catalyzed hydrolysis of α-Glc 1-P where the C1-O bond is broken and water is incorporated to the anomeric glucosyl carbon, the phosphatase reaction is expected to result in water addition to phosphorus. Measurement of $^{18}$O label incorporation from an isotopically enriched water solvent is therefore useful to distinguish between the two mechanistic possibilities. Enzymatic conversions of 2.0 mM α-Glc 1-P were carried out in H$_2$18O (90% $^{18}$O content in the final reaction mixture) and in normal water (control). α-Glc 1-P was depleted fully in each reaction. GC-MS analysis was used to determine the isotopic composition of the phosphate released. A tris(trimethylsilyl) phosphate (TMS-phosphate) species was analyzed. Under electron ionization conditions as described in literature (62) and confirmed in our experiments, the TMS-phosphate molecular ion at m/z 314 fragments due to loss of one methyl group and major ion at m/z 299 is formed. Full analytical details along with the experimental GC-MS chromatograms were analyzed. Reactions in normal water gave a peak area ratio of 0.13, which is consistent with the natural $^{18}$O/$^{16}$O isotope ratio in phosphate calculated with IsoPro 3.1. Reactions in $^{18}$O-enriched solvent gave much larger peak area ratios (up to 65-fold increase) than the corresponding controls, clearly indicating $^{18}$O label incorporation from solvent to phosphate under these conditions. A mechanistic control was performed where sucrose phosphorylase was incubated with α-Glc 1-P in H$_2$$^{18}$O solvent. α-Glc 1-P was hydrolyzed by the phosphorylase without detectable labeling of the phosphate released, as expected from the catalytic mechanism. Therefore, these results strongly support the notion that enzymatic hydrolysis of α-Glc 1-P by α-Glc 1-P phosphatase proceeds via the canonical phosphomonoester hydrolase mechanism where bond cleavage and formation occurs at phosphorus, as shown in FIG. 2.

Example 3: Phosphoryl Transfer Studies

Phosphoryl Transfer Studies.

Reactions were performed as described above (Phosphatase kinetics) using 20 mM α-Glc 1-P as the donor substrate. Fru (100, 200, 400 or 600 mM) or Glc (200 mM) was used as the acceptor substrate. Samples taken at certain times were analyzed for phosphate, αGlc 1-P, and Glc 6-P. When Fru was the acceptor, Fru 1-P and Fru 6-P were additionally measured in each sample. Sampling was done to allow for determination of initial rates, but the full reaction time course was also recorded. Relevant $k_{cat\_app}$ values for substrate consumption, phosphate release, and phosphoryl transfer were obtained from the corresponding V values using equation 2. Internal consistency of the data was always checked by mass balance. pH dependence of phosphoryl transfer. Reactions (0.1 μM enzyme) contained 20 mM of each αGlc 1-P and Fru, and $k_{cat\_app}$ was determined from V for consumption of αGlc 1-P or formation of Fru 1-P. The pH range analyzed was 4.0-8.0. A 50 mM Mes buffer was used, except at pH ≤6.0 where 50 mM Mes and 20 mM sodium acetate were used, and at pH 8.0 where 50 mM Mes and 50 mM Tes were used. Buffer pH values were adjusted at 37° C. and controlled before and after recording each enzyme-catalyzed reaction. Sampling and analyses were as described above.

For data analysis by non-linear least-squares regression, SigmaPlot 2004 version 9.0 was used. Equation 3 describes a pH dependence where activity (expressed as logarithmic $k_{cat\_app}$) is constant at low pH and decreases above p$K_B$. C is the pH-independent value of $k_{cat\_app}$ at the optimum state of protonation, K is the proton dissociation constant and [H$^+$] is the proton concentration.

$$\log(k_{cat\_app})=\log(C/(1+K/[H^+])) \quad (3)$$

High Performance Anion Exchange Chromatography with Pulsed Amperometric Detection (HPAEC-PAD).

Selected samples were analyzed on a Dionex BioLC system (Dionex Corporation, Sunnyvale, USA) equipped with a CarboPac PA10 column (4×250 mm) and an Amino Trap guard column (4×50 mm) thermostated at 30° C. Glc, Fru, αGlc 1-P, Glc 6-P, Fru 1-P and Fru 6-P were detected with an ED50A electrochemical detector using a gold working electrode and a silver/silver chloride reference electrode, applying the predefined waveform for carbohydrates. Elution was carried out at a flow rate of 0.9 mL/min with the following method: isocratic flow of 52 mM NaOH for 20 min, followed by a linear gradient from 100 mM NaOAc to 400 mM NaOAc, applied within 25 min in an isocratic background of 100 mM NaOH. The column was washed for 5 min with 52 mM NaOH. Under the conditions applied, Glc eluted after 10.2 min, Fru after 11.8 min, αGlc 1-P after 30.3 min, Glc 6-P after 36.6 min, Fru 1-P after 37.2 min and Fru 6-P after 39.1 min.

NMR Spectroscopic Measurements.

For sample preparation, 20 mM αGlc 1-P and 200 mM Fru were incubated with 0.1 μM αGlc 1-P phosphatase at 37° C. for 75 min. The reaction was stopped by heating (99° C., 5 min). After centrifugation at 20,000 g for 5 min, the supernatant was applied on a DEAE FF column (GE Healthcare, Little Chalfont, U.K.), pre-equilibrated with deionized water. Unbound, non-charged monosaccharides were removed by washing with deionized water. Elution of phosphorylated reaction products was accomplished by using 50 mM NaCl. Fractions containing the phosphorylated product were pooled and concentrated by lyophilisation, prior to NMR analysis.

For NMR analysis, the isolated compound was dissolved in $D_2O$ (~5 mg in 0.7 mL) and transferred into 5 mm high precision NMR sample tubes. Measurements were performed on a Bruker DRX-400 at 400.13 MHz ($^1H$) using the Topspin 1.3 software. 1D $^1H$ NMR spectra were recorded by acquisition of 64 k data points and Fourier transformation resulting in spectra with a range of 14 ppm. To determine the 2D COSY, TOCSY, and NOESY spectra 128 experiments with 2048 data points each were recorded and Fourier transformed to 2D-spectra with a range of 10 ppm. Measurement temperature was 298 K+/−0.05 K and external acetone was used as shift reference standard ($\delta_H$ 2.225).

Isolated Compounds.

β-D-fructopyranose 1-phosphate-$^1H$ NMR ($D_2O$): δ=3.99 (1H, m, H-6a), 3.93 (1H, m, H-3), 3.84 (1H, m, H-4*), 3.82 (1H, m, H-1b), 3.81 (1H, m, H-1a), 3.77 (1H, m, H-5*), 3.65 (1H, m, H-6b); $^{13}C$ NMR ($D_2O$): δ=96.3 (s, C-2), 71.9 (d, C-3), 71.8 (d, C-4*), 70.5 (d, C-5*), 68.6 (t, C-6), 66.2 (t, C-1); $^{31}P$ NMR ($D_2O$): δ=5.5 (RO—$POH_2^-$); other isomers regarding anomeric form and pyrano/furano form are present in negligible concentrations; [*] shifts are not unequivocally assignable.

Molecular Docking Studies.

AutoDock 4.2 as implemented in Yasara V 11.11.21 was used for enzyme-ligand docking. The AMBER03 force field and the default parameters provided by the standard docking macro were used, except that the number of runs was increased to 50. The structure of αGlc 1-P phosphatase (His[18]→Ala mutant; pdb entry 1nt4) was used as macromolecule in molecular docking experiments that employed αGlc 1-P or αGlc 6-P, each as di- or mono-anion, as the ligand. 3D coordinates of the ligands were generated from SMILES strings using Chimera (www.cgl.ucsf.edu/chimera). Docking was performed with Asp[290] protonated or unprotonated. The ligand was placed flexible into the enzyme active site that was covered completely by the applied search space of 15×10×10 Å. Docking poses were evaluated by their associated free energy and mechanistic plausibility. PyMOL (www.pymol.org) was used for visualization.

Phospho-Donor Substrate Utilization by αGlc 1-P Phosphatase in Hydrolysis.

A series of phosphorylated sugars were tested as substrates for hydrolysis by phosphatase. Apparent turnover frequencies ($k_{cat\_app}$) determined at 20 mM substrate concentration were summarized in Table 3. The enzyme exhibited high selectivity for hydrolyzing α-Glc 1-Pas compared to β-Glc 1-P, which was completely inactive towards αGlc 1-P phosphatase. Phospho-sugars harboring the phosphomonoester group at a primary hydroxyl (Glc 6-P; Fru 6-P; D-fructose 1-phosphate, Fru 1-P) were utilized with high activity, the respective $k_{cat\_app}$ being comparable within a 2-fold range to the $k_{cat\_app}$ for conversion of α-Glc 1-P. Pyrophosphate and phytate (myo-inositol hexakisphosphate) were also examined as enzyme substrates, and reactions were performed at pH 7.0 and pH 4.5 (50 mM sodium acetate). Pyrophosphate was not hydrolyzed which is interesting because it is an excellent substrate for many acid phosphatases (39, 63). α-Glc 1-P phosphatase was weakly active with phytate, but only at the low pH of 4.5 where the phytate is no longer strongly complexed with metal ions (64).

Phosphorylation of Different Sugar Substrates.

Figure 5:
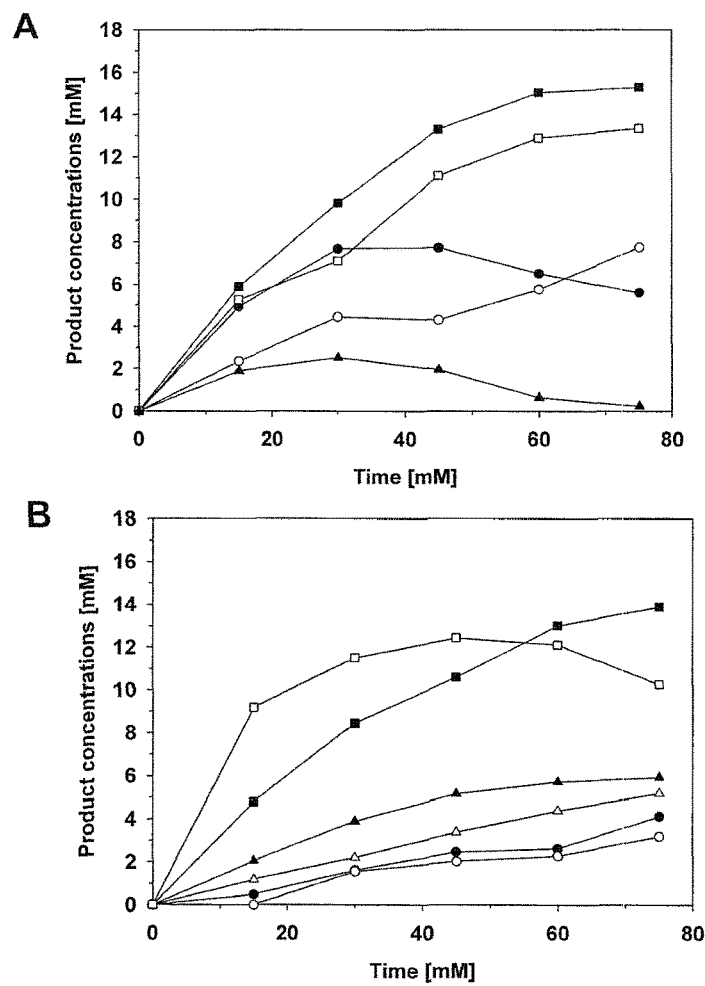
FIG. 5: Product formation catalyzed by αG1Pase. (A) (■) D-Fructose (□) D-glucosamine (●) D-galactose (○) N-acetyl glucosamine (▲) L-fucose (B) (□) D-Mannose (■) L-sorbose (Δ) D-xylose (▲) L-arabinose (○) D-xylitol (●) L-arabitol.

Phosphorylation of different acceptors catalyzed by α-Glc 1-P phosphatase using α-Glc 6-P as donor substrate were performed in 50 mM Mes pH 7.0 supplemented with 20 mM α-Glc 6-P and 200 mM of the respective acceptors. The product formation in dependence of time is shown in FIG. 5.

Enzymatic Transphosphorylation: αGlc 1-P Phosphatase Catalyzes Efficient Phosphoryl Transfer from αGlc 1-P to the 6-Hydroxyl of an External Glc Acceptor.

During time-course studies of hydrolysis of αGlc 1-P (20 mM) by αGlc 1-P phosphatase, in a late phase of the reaction (≥70% substrate conversion), the molar concentration of phosphate released did not match up exactly (≥10%) to the α-Glc 1-P consumed. Analysis of the reaction mixture by HP anion exchange chromatography with pulsed amperometric detection (HPAEC-PAD) revealed the presence of a new phosphorylated sugar, which was found to co-elute with an authentic Glc 6-P standard. The presence of Glc 6-P in the reaction sample was confirmed unambiguously using an enzymatic assay based on selective $NAD^+$ dependent oxidation of Glc 6-P by Glc 6-P dehydrogenase. The amount of Glc 6-P formed accounted precisely for the phosphate missing in the balance with αGlc 1-P converted. The synthesis of Glc 6-P during conversion of αGlc 1-P was suggested to have resulted from an enzymatic transphosphorylation reaction in which αGlc 1-P was the donor, and the Glc formed in prior hydrolysis was the acceptor. Mechanistically, the substrate's phosphoryl group would be transferred to the catalytic His[18] of the enzyme, and dephosphorylation of αGlc 1-P phosphatase could then occur by reaction with water (hydrolysis) or Glc (phosphoryl transfer). Because phosphoryl transfer would take place in competition with hydrolysis, the Glc concentration is decisive for efficient utilization of αGlc 1-P for synthesis of Glc 6-P.

Figure 6:
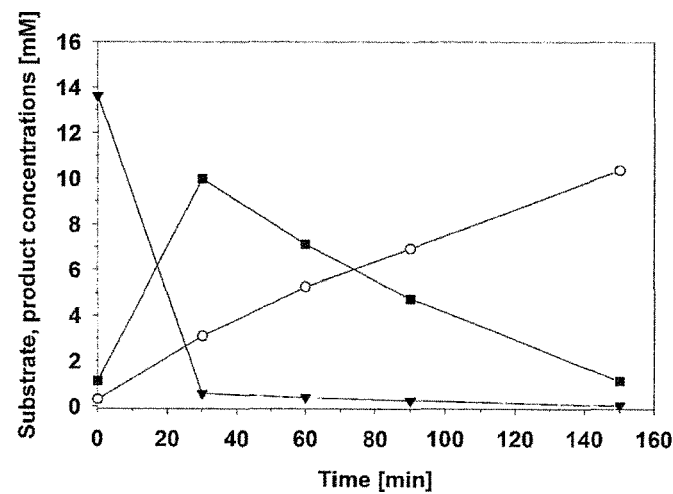
FIG. 6: Time-course for the synthesis of Glc 6-P from αGlc 1-P and Glc catalyzed by αGlc 1-P phosphatase. The reaction mixture contained 20 mM αGlc 1-P, 200 mM Glc and 0.1 μM αGlc 1-P phosphatase in 50 mM Mes, pH 7.0. Symbols indicate: αGlc 1-P (▼), Glc 6-P (■) and phosphate (○).

The enzymatic conversion of αGlc 1-P (20 mM) was therefore repeated with 200 mM Glc added as external phosphoryl acceptor at reaction start. FIG. 6 shows Glc 6-P production in relation to αGlc 1-P consumption along time courses of reaction catalyzed by αGlc 1-P phosphatase.

Formation of free phosphate is also shown. Using α-Glc 1-P phosphatase, Glc 6-P was formed in large amounts, accounting for nearly all of the αGlc 1-P cleaved in the enzymatic reaction. Compared to the control reaction lacking Glc, the phosphate release rate was suppressed to a large extent (~10-fold). The $k_{cat\_app}$ of phosphate formation was just 4 s$^{-1}$ under these conditions. Data in FIG. 6 were furthermore used to calculate $k_{cat\_app}$ values of 34 s$^{-1}$ and 40 s$^{-1}$ for Glc 6-P synthesis and α-Glc 1-P consumption, respectively. Apparent turnover frequencies for the overall conversion were therefore similar in the absence and presence of Glc. Conversion of αGlc 1-P into Glc 6-P is formally equivalent to the phosphoglucomutase reaction, which however involves positional rearrangement of the phosphomonoester group within the same glucose molecule between O6 and α-O1 (7). Equilibrium of the phosphoglucomutase reaction strongly favors Glc 6-P (65). Synthesis of Glc 6-P by enzymatic transphosphorylation proceeded through a kinetic optimum of about 10 mM Glc 6-P (FIG. 6). At longer reaction times, Glc 6-P was hydrolyzed completely.

Synthesis of Fru 1-P by enzymatic transphosphorylation from Glc 1-P.

Figure 7:
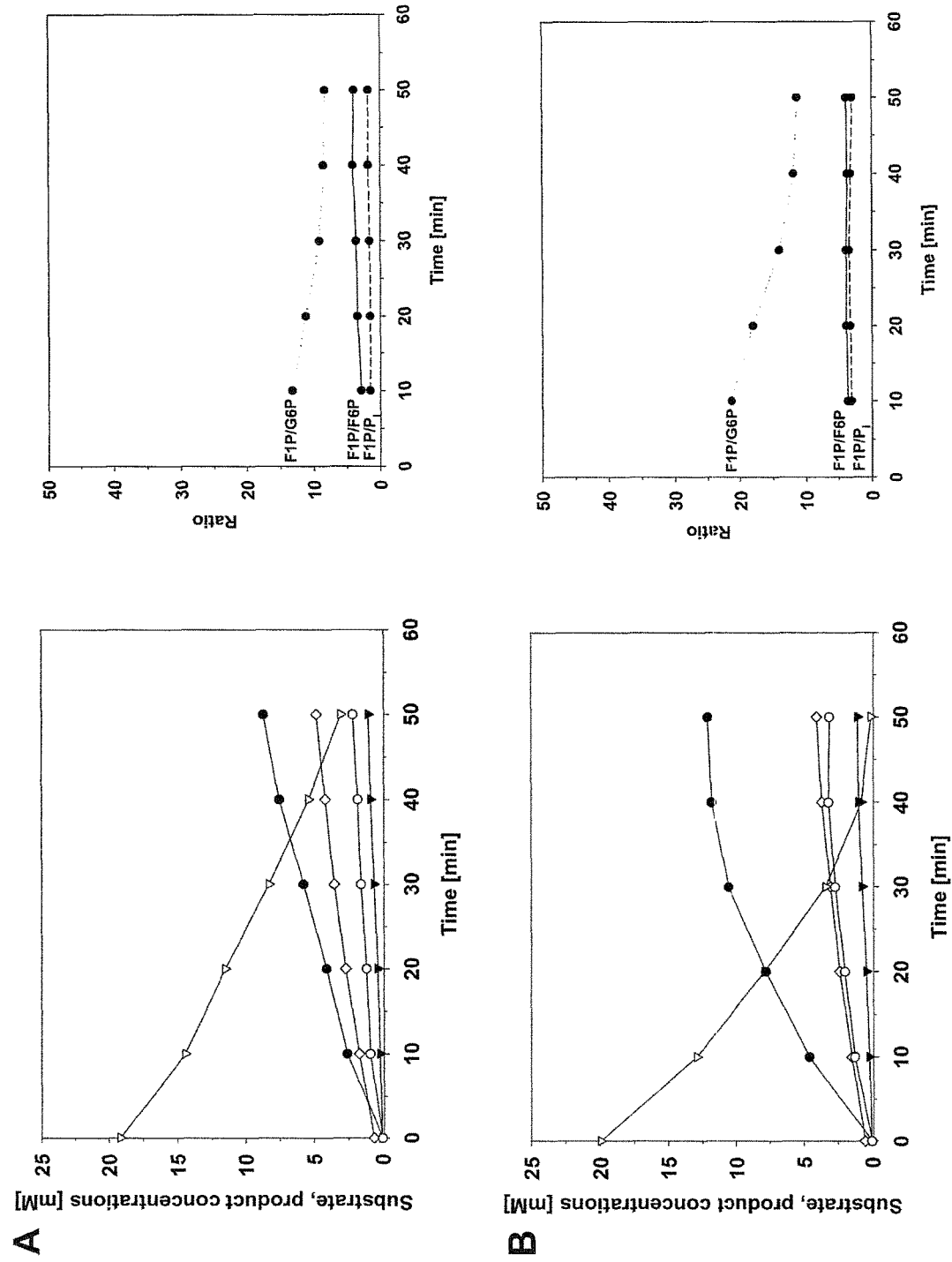
FIG. 7: Time-courses for Fru 1-P (●) production from 20 mM αGlc 1-P (∇) in the presence of 100 mM (A), 200 mM (B), 400 mM (C), and 600 mM Fru (D), respectively. The formation of side products, Glc 6-P (▼), Fru 6-P (○), and phosphate (◇) is indicated. The ratios of Fru 1-P to Glc 6-P (F1P/G6P), Fru 1-P to Fru 6-P (F1P/F6P) and Fru 1-P to hydrolysis (F1P/Pi), displayed on the right panel, are extracted from the corresponding time courses displayed on the left.
Figure 7:
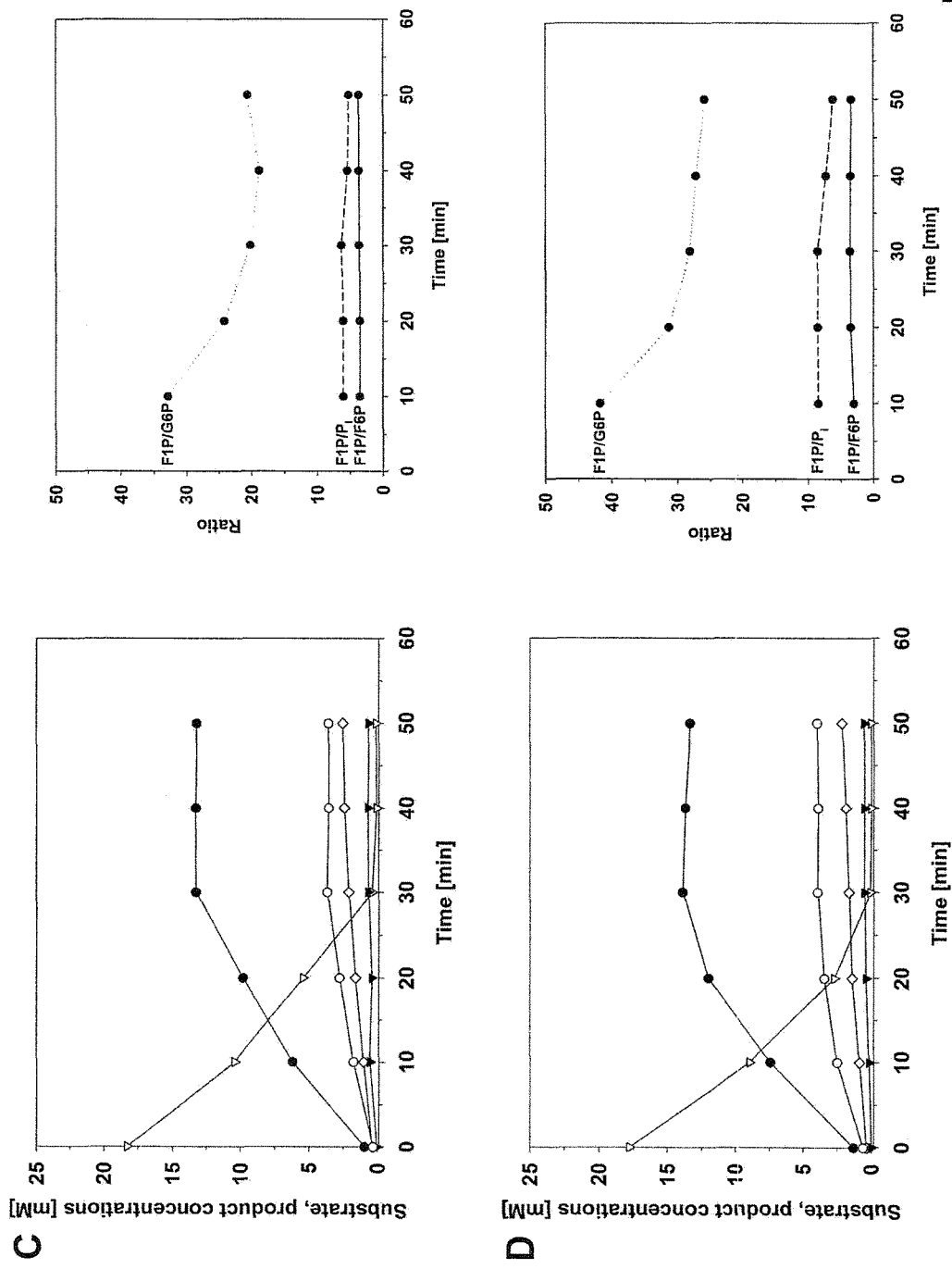
Figure 8:
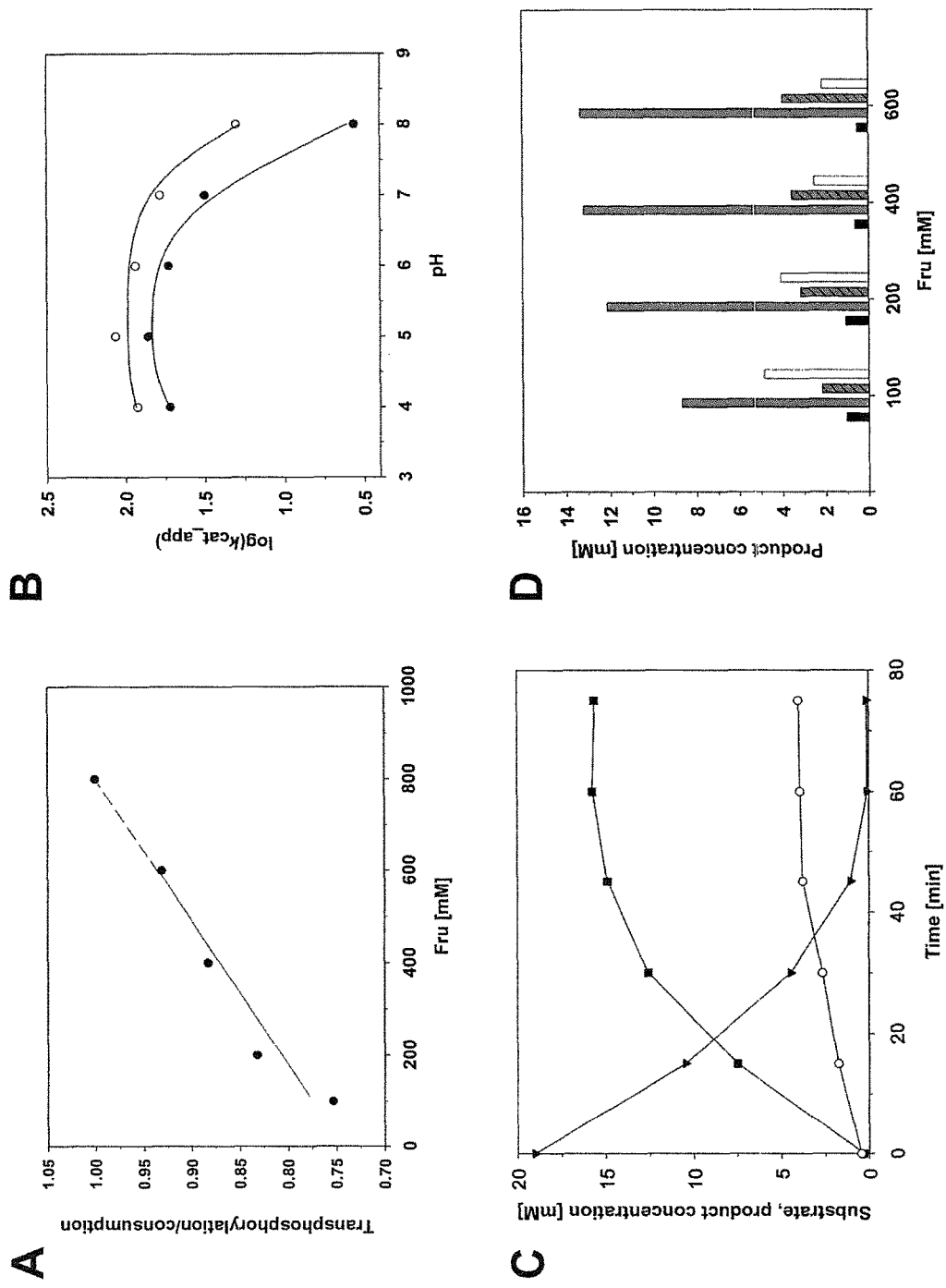
FIG. 8: Kinetic study of the hydrolysis-transphosphorylation reaction catalyzed by αGlc 1-P phosphatase. (A) The ratio of the total transphosphorylation rate (Fru 1-P, Fru 6-P, Glc 6-P) and the αGlc 1-P consumption rate in dependency on the Fru concentration (100 mM-600 mM; solid line). The ratio approaches a value of unity at high Fru concentrations, as indicated by the dashed line. (B) pH dependencies of logarithmic $k_{cat\_app}$ for αGlc 1-P consumption (○) and Fru 1-P synthesis (●). Lines are fits of equation 3 to the data. (C) A complete time course of conversion of 20 mM αGlc 1-P in the presence of 200 mM Fru. Symbols indicate: αGlc 1-P (▼), sum of phosphorylated products (■) and phosphate (○). (D) Phosphorylated products synthesized in transphosphorylation reactions performed at different initial concentrations of Fru at 50 min. Fru 1-P (grey), Glc 6-P (black), Fru 6-P (grey dashed), phosphate (white).

When Fru (200 mM) was added to conversions of α-Glc 1-P (20 mM) by α-Glc 1-P phosphatase, there was the interesting effect that compared to the control reaction performed in the absence of Fru the α-Glc 1-P consumption rate was enhanced about 3-fold ($k_{cat\_app}$=137 s$^{-1}$) whereas the phosphate release rate was decreased about 2-fold at the same time ($k_{cat\_app}$=18 s$^{-1}$). Therefore, this provided clear indication that phosphoryl transfer from αGlc 1-P to an acceptor other than water, likely Fru, constituted the major route of phosphoryl donor substrate utilization under the conditions used. Using analysis by HPAEC-PAD, formation of new sugar phosphate products was confirmed. Comparison of $k_{cat\_app}$ under hydrolysis-only and phosphoryl transfer conditions revealed that α-Glc 1-P phosphatase was somehow "activated" in the presence of external acceptor. In the proposed scenario of enzymatic transphosphorylation where an otherwise hydrolyzed phospho-enzyme intermediate is intercepted by acceptor, enhancement of $k_{cat\_app}$ in the presence of Fru is possible when enzyme dephosphorylation is a slow step of the overall hydrolysis process, and is accelerated by the reaction with Fru. Consistent with this notion, it was shown that $k_{cat\_app}$ (α-Glc 1-P) increased about 5-fold in hyperbolic dependence of the Fru concentration (100-600 mM; Table 4), approaching a calculated maximum value of 254 s$^{-1}$ at saturating concentrations of the phosphoryl acceptor (FIG. 7). An apparent $K_M$ for Fru of 209 mM was determined from the data. Table 4 summarizes results of comprehensive kinetic analysis of enzymatic transphosphorylations at different Fru acceptor concentrations. Expressed in apparent first-order rate constants, the phosphate release rate was suppressed strongly in the presence of acceptor, to less than one-tenth the α-Glc 1-P consumption rate under conditions of 600 mM Fru. Formation of Glc 6-P occurred at a very low rate. Synthesis of Fru 6-P took place at about one-fourth the rate of Fru 1-P formation, irrespective of the Fru concentration used. In FIG. 8A the ratio of the total transphosphorylation rate (Fru 1-P, Fru 6-P, Glc 6-P) and the α-Glc 1-P consumption rate are plotted and its dependence of the Fru concentration is shown. The ratio approached a value of unity at high Fru, consistent with the mechanistic notion that externally added (Fru) and in situ formed (Glc) acceptors compete effectively with water for reaction with the phospho-enzyme intermediate. Various phosphatases related to αGlc 1-P phosphatase by common membership to the histidine acid phosphatase family of proteins exhibit their optimum activity in the acidic pH range (≤5.0) (66, 67). pH dependencies of $k_{cat\_app}$ for αGlc 1-P consumption and Fru 1-P synthesis by α-Glc 1-P phosphatase in the pH range 4.0-8.0 were therefore determined. Activity was constant in the pH range 4.0-6.0 and gradually decreased at higher pH. Activity at the standard pH of 7.0 was still 88% of the activity at optimum pH. Interestingly, the pH-rate profiles for αGlc 1-P consumption and Fru 1-P synthesis were identical (FIG. 8B), indicating that partitioning of the phospho-enzyme intermediate between reaction with Fru and reaction with water is not dependent on pH.

TABLE 4

Kinetic analysis of transphosphorylation by αGlc 1-P phosphatase analyzed at different Fru concentrations. The S.D. for $k_{cat\_app}$ was ≤10% of the reported value, except $^a$11%, $^b$16%, and $^c$20%.

| Fru [mM] | Glc 1-P $k_{cat\_app}$ [s$^{-1}$] | Fru 1-P $k_{cat\_app}$ [s$^{-1}$] | Glc 6-P $k_{cat\_app}$ [s$^{-1}$] | Fru 6-P $k_{cat\_app}$ [s$^{-1}$] | Phosphate $k_{cat\_app}$ [s$^{-1}$] |
|---|---|---|---|---|---|
| 0 | 40 | n.a. | n.a. | n.a. | 40 |
| 100 | 73 | 39 | 5 | 11$^b$ | 21 |
| 200 | 137 | 88 | 6 | 20 | 18 |
| 400 | 162 | 111$^a$ | 4 | 28 | 14 |
| 600 | 189 | 135 | 5 | 36$^c$ | 13 |

Not applicable, n.a.

A complete time course of conversion of α-Glc 1-P in the presence of 200 mM Fru is shown in FIG. 8C. From the phosphate concentration present at the time when α-Glc 1-P was completely exhausted the total concentration of transphosphorylation product(s) was determined as 16 mM, corresponding to a yield of 80% based on donor substrate utilized. Using HPAEC-PAD analysis referenced against authentic standards, it was shown that Fru 1-P was the main product (12 mM), and Fru 6-P (2.7 mM) and Glc 6-P (1.0 mM) were formed as by-products. However, Glc 6-P appeared mainly in the late phase of the reaction when substantial concentrations of Glc (≥10 mM) had already accumulated. The molar ratio of Fru 1-P to Glc 6-P decreased during the reaction from an initial value of 20 to about 10 at conversion end (FIG. 7). Phosphorylation of Glc occurred despite Fru being present in about 20-fold molar excess, reflecting the acceptor substrate selectivity of αGlc 1-P phosphatase. In spite of the pronounced hydrolase activity of αGlc 1-P phosphatase towards each sugar phosphate synthesized in the reaction (Table 3), no loss of transphosphorylation product to secondary hydrolysis occurred in the timespan of the experiment. Unlike other phosphatase-catalyzed transphosphorylation reactions in which product kinetic stability presented a problem to synthetic application of the biocatalytic transformations (37, 38), sugar phosphates were formed from α-Glc 1-P as if they were real equilibrium products (FIG. 8C), thus enabling their convenient production. FIG. 8D shows the composition of phosphorylated products obtained from conversion of αGlc 1-P at different Fru concentrations.

Identity of Fru 1-P was further confirmed through 1D and 2D NMR analysis of the product 1c) mixture. Fru 1-P was present in four different anomeric forms, whereby the β-D-fructopyranose 1-phosphate had highest abundance (~80%). For this anomer, the proton signals of H-1a&b resonated as separated signal group in an ABX at 3.82 ppm and 3.81 ppm with a $^3J_{H-P}$ heteronuclear coupling to the phosphate group. All other proton signals belonged to spin system, as detected in the TOCSY spectrum. The proton signals of the methylene group in position 6 were present at 3.99 and 3.65 ppm, both showing $^3J_{H\text{-}H}$ couplings to H-5, which resonated at 3.77 ppm. Further coupling of H-5 to H-4 (3.84 ppm) and consecutively of H-4 to H-3 (3.95) were also visible in COSY spectra. The large shift difference between signals of H-6a and H-6b indicated the anomeric form. Furthermore, NMR data of the enzymatically synthesized Fru 1-P were in exact agreement with reference spectra recorded from commercial Fru 1-P. The NMR data combined with evidence from HPAEC-PAD analysis and enzymatic assays confirmed Fru 6-P and Glc 6-P to be transphosphorylation products next to Fru 1-P.

Binding of αGlc 1-P and Glc 6-P by αGlc 1-P Phosphatase Analyzed by Molecular Docking.

The x-ray crystal structure of α-Glc 1-P phosphatase having the catalytic His[18] substituted by Ala contains a bound ligand reported to be α-Glc 1-P (45). However, the phospho-sugar represented by the atomic coordinates of the enzyme-ligand complex is clearly β-Glc 1-P, not α-Glc 1-P. An experimental electron density map was not released with the protein structure and cannot therefore be used for clarification. Docking studies were performed in which α-Glc 1-P was placed flexible into the substrate binding pocket of the enzyme (pdb entry 1 nt4). Binding of singly or doubly negatively charged α-Glc 1-P was examined, and the putative catalytic acid-base Asp[290] was analyzed protonated or unprotonated. The best-fit docking poses received under the different conditions were independent of the charge state of α-Glc 1-P and Asp[290]. α-Glc 1-P is accommodated in an elongated conformation with the phosphoryl group placed anti relative to the glucosyl moiety. The substrate's glycosidic oxygen O1 is brought into a position that would allow protonated Asp[290] to provide Brønsted catalytic assistance to O1-P bond fission and thus to the departure of the Glc leaving group. Asp[290] could adopt an analogous catalytic role during hydrolysis of β-Glc 1-P, even though the distance between the catalytic enzyme and the reactive substrate groups is substantially larger (3.4 Å) than in the α-Glc 1-P docking pose (2.9 Å). 3-Glc 1-P is not a substrate of α-Glc 1-P phosphatase (Table 3), and the binding mode of β-Glc 1-P in the protein crystal structure may actually be non-productive for catalysis to O1-P bond cleavage. Evidence from the docking analysis indicates that substrate binding recognition by α-Glc 1-P phosphatase is mainly through numerous strong interactions with the phosphoryl group whereas the glucosyl moiety of α-Glc 1-P is bound only weakly by comparison. The docking experiments resulted in up to 6 docking poses of similar calculated free energies. The different docking poses had the phosphoryl group bound similarly, but featured variation in the alignment of the glucosyl moiety. Size and topology of the binding pocket appear adequate for accommodation of different sugar structures in multiple orientations, as shown for binding of Glc 6-P compared to binding of α-Glc 1-P, thus explaining the relaxed donor and acceptor substrate specificity of the enzyme. It is not practical to examine transphosphorylation compared to hydrolysis reaction selectivity using molecular docking.

Molecular and Kinetic Properties of αGlc 1-P Phosphatase Underlying the Enzyme's Remarkable Transphosphorylation Activity.

α-Glc 1-P phosphatase catalyzed hydrolysis of different sugar phosphates with relaxed specificity for the structure of the leaving group (Glc, Fru) and for the position of the phosphoryl group on the sugar moiety (α-Glc 1-P, Glc 6-P). In a comparison of the α and 3-anomers of Glc 1-P, however, the enzyme discriminated strongly against hydrolysis of 3-Glc 1-P. Docking analysis carried out on the x-ray crystal structure of α-Glc 1-P phosphatase suggested a molecular basis for the anomeric selectivity of the enzyme. It also provided interpretation of the broad donor and acceptor substrate specificity of α-Glc 1-P phosphatase.

Incorporation of $^{18}O$ label from $H_2^{18}O$ solvent into the phosphate released during hydrolysis of αGlc 1-P by αGlc 1-P phosphatase supports enzymatic reactions through nucleophilic substitution at the phosphorus. According to mechanistic proposals for histidine acid phosphatases (FIG. 2), the overall conversion of α-Glc 1-P is expected to proceed in a two-step double displacement-like catalytic process via a covalent phospho-histidine and phospho-aspartate enzyme intermediate, respectively. Phosphoryl transfer to sugar acceptors occurs from the phosphorylated enzyme, probably after dissociation of the Glc, in direct competition to hydrolysis. Efficient interception of the phospho-enzyme intermediate to prevent its reaction with water will therefore be key characteristic of synthetically useful acceptor substrates. Partitioning of the phosphorylated enzyme to catalytic break-down via phosphoryl transfer and hydrolysis is adjustable by the acceptor substrate concentration, as shown for the phosphorylation of Fru by α-Glc 1-P phosphatase (FIG. 8A). Using the data from conversion of α-Glc 1-P in the presence of 200 mM Glc, the experimental $k_{cat\_app}$ ratio for formation of Glc 6-P and phosphate can be applied to calculate that αGlc 1-P phosphatase ($k_{cat\_app}$ ratio=34/4.0=8.5). With current bioinformatic methodology it is not possible to infer the catalytic ability of transphosphorylation from a phosphatase protein structure alone, therefore necessitating the dedicated biochemical characterization. Acceptor substrate selectivity and phosphorylation site selectivity of transphosphorylation will be fine-tuned by positioning of the sugar acceptor substrate in the binding pocket on the phospho-enzyme intermediate. αGlc 1-P phosphatase accommodated Fru in two distinct binding modes, where the preferred binding mode resulted in formation of Fru 1-P, and the other resulted in formation of Fru 6-P.

Synthetic Use of Transphosphorylation from αGlc 1-P.

Fru 1-P is a high-value metabolite that is difficult to synthesize chemically (68). Biocatalytic synthetic routes to Fru 1-P are aldolase (EC 4.1.2.13)-catalyzed carbon-carbon coupling between glyceraldehyde and dihydroxyacetone phosphate (69), or 1-phosphorylation of Fru from ATP by keto-hexokinase (EC 2.7.1.3) (62, 63). Transphosphorylation from α-Glc 1-P presents an interesting alternative that offers the advantage of a convenient and cheap phosphoryl donor substrate compared with ATP or dihydroxyacetone phosphate. Moreover, α-Glc 1-P phosphatase showed excellent turnover frequency ($\geq 100$ s$^{-1}$; Table 4) for transphosphorylation between αGlc 1-P and Fru. By employing Fru at 600 mM, utilization of αGlc 1-P as donor substrate for transphosphorylation was almost complete in a sense that substrate hydrolysis was prevented effectively ($\geq 10\%$; see FIG. 7). Based on αGlc 1-P converted, Fru 1-P was obtained in 70% yield (14 mM). Remainder products were Fru 6-P (4 mM) and Glc 6-P (0.5 mM). It would be interesting to increase the initial αGlc 1-P concentration in a next step of optimization of the biocatalytic phosphorylation of Fru for synthesis of Fru 1-P. Efficient methodology for chromatographic separation of phospho-sugars has been developed (70, 71) so that capture of the Fru 1-P from product mixture with Fru 6-P and Glc 6-P is certainly possible. Alternatively, selective hydrolysis of the sugar 6-phosphates using a primarily hydrolytic phosphatase (72) might be useful.

Following the early discovery of phosphoryltransferase activity in certain phosphatases (36), recent work has demonstrated the synthetic usefulness of biocatalytic transphosphorylation reactions in the preparation of different sugar phosphates. Bacterial phosphatases from the class-A nonspecific acid phosphatase family were mostly used, and *Shigella flexneri* (37, 73), *Salmonella enterica* (73) and *Morgenella morganii* (74) were prominent sources of the enzyme. A key paper of Wever and colleagues showed phosphorylation of a series of aldohexose, aldopentose, and ketohexose acceptors from a pyrophosphate donor substrate using acid phosphatase from *S. flexneri* (37). Using donor and acceptor at 100 mM each, the yield of phosphorylated product was typically 15% or lower, except for the 6-phosphates of Glc and 5-thio-D-glucose that were obtained in substantially higher yields. Interestingly, Fru was a rather poor acceptor substrate for the *Shigella* phosphatase (5% phosphorylation yield), suggesting useful complementarity in the acceptor substrate specificities of α-Glc 1-P phosphatase and the previously used transphosphorylation catalyst. Moreover, whereas the nonspecific acid phosphatases were used at pH 4.0, α-Glc 1-P phosphatase can also be applied in the neutral pH range. Using aldohexose acceptors (e.g. Glc, D-mannose, D-galactose), it was shown by van Herk et al. (37) that the maximum concentration of phosphorylated product obtained from 100 mM pyrophosphate was strongly dependent on the acceptor concentration used; and that it went through a distinct kinetic optimum due to the pronounced effect of secondary hydrolysis at extended reaction times. Glc 6-P was an exception and it was obtained as a kinetically stable transphosphorylation product. Problems with secondary hydrolysis were not encountered during αGlc 1-P phosphatase-catalyzed phosphorylations of Fru. However, Glc 6-P was hydrolyzed. Finally, even though pyrophosphate is generally viewed as a highly expedient phosphoryl donor substrate for enzymatic transphosphorylations, it must not be overlooked that even in the absence of hydrolysis, the pyrophosphate conversion results in the release of inorganic phosphate, which can inhibit the phosphatase (40). The use of α-Glc 1-P in combination with a dedicated α-Glc 1-P phosphatase might help minimizing the effect of product inhibition by phosphate in phosphatase-catalyzed transphosphorylation reactions. The enzyme from *E. coli* α-Glc 1-P phosphatase is a powerful biocatalyst for this type of transformation.

Example 4: Phosphylation Using a Phosphorylase-Phosphatase Biocatalyst

Figure 9:
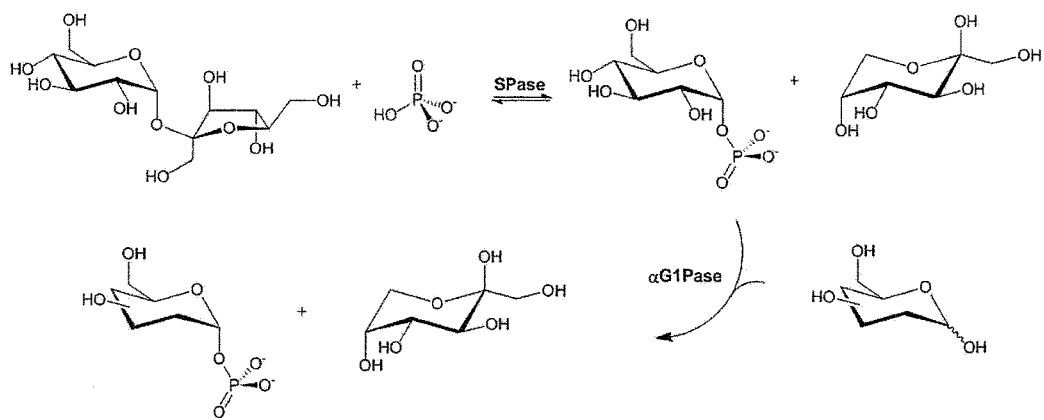
FIG. 9: Synthesis of α-glycosyl phosphates by combi-biocatalyst of sucrose phosphorylase (SPase) and α-Glc 1-P phosphatise (α-G1Pase).

Simultaneous and sequential two-step transformations as shown in FIG. 9 by a phosphorylase-phosphatase biocatalyst yielded α-aldose 1-phosphate and ketose 1-phosphate products in typically excellent yields of ≥70% based on the phosphate applied to the reaction. Glucosylation from sucrose was thermodynamically efficient (~80% yield) in activating phosphate for the subsequent phosphoryl transfer. Using the hexose/ketose acceptor in suitable concentration, phosphatase-catalyzed hydrolysis of α-D-glucose 1-phosphate was strongly suppressed.

Figure 10:
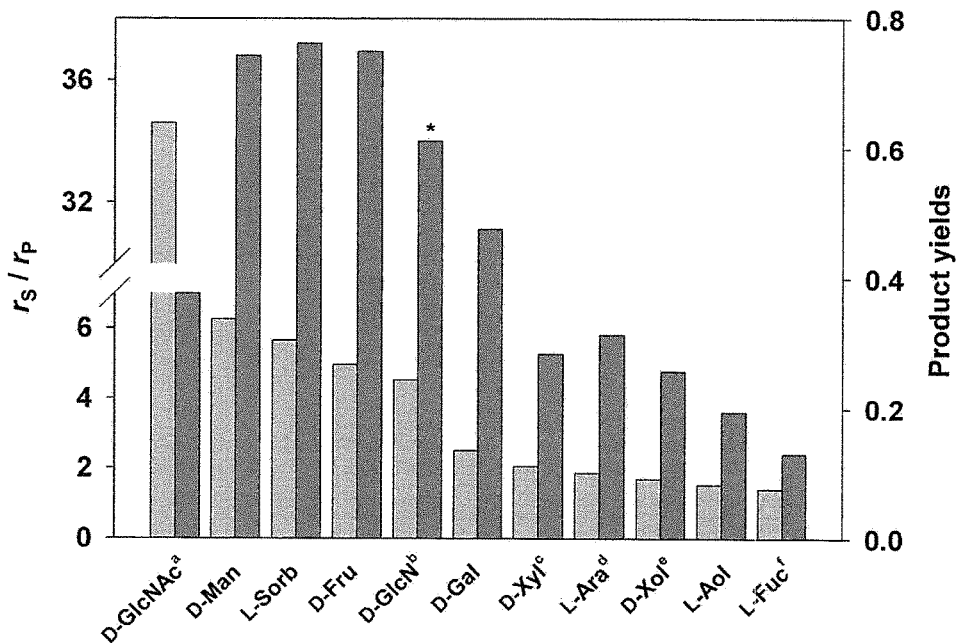
FIG. 10: Acceptor substrates phosphorylated by glucose-1-phosphatase. The αGlc 1-P consumption rate ($r_S$) to phosphate release rate ($r_P$) ratio was determined for each acceptor. D-Glucuronic acid and D-galactosamine were not phosphorylated by glucose-1-phosphatase. Product yields were determined at conversions >90% except for N-acetyl D-glucosamine (GlcNAc) 38%, D-glucosamine (D-GlcN) 81%, D-xylose (D-Xyl) 69%, L-Arabinose (L-Ara) 86%, D-Xylitol (D-Xol) 89% and L-Fucose (L-Fuc) 75%, respectively. All acceptors are phosphorylated at the C1-OH position except for (*) D-glucosamine where the predominant product was phosphorylated at the C6-OH. Light grey bars indicate $r_S/r_P$ ratio, while the dark grey bars indicate the product yield. Reactions contained 20 mM αGlc 1-P and 200 mM acceptor.

Acceptor substrates phosphorylated by glucose-1-phosphatase are shown in FIG. 10. The αGlc 1-P consumption rate ($r_s$) to phosphate release rate ($r_p$) ratio was determined for each acceptor. D-Glucuronic acid and D-galactosamine were not phosphorylated by glucose-1-phosphatase. Product yields were determined at conversions >90% except for N-acetyl D-glucosamine (GlcNAc) 38%, D-glucosamine (D-GlcN) 81%, D-xylose (D-Xyl) 69%, L-Arabinose (L-Ara) 86%, D-Xylitol (D-Xol) 89% and L-Fucose (L-Fuc) 75%, respectively. All acceptors are phosphorylated at the C1-OH position except for (*) D-glucosamine where the predominant product was phosphorylated at the C6-OH. Light grey bars indicate $r_s/r_p$ ratio, while the dark grey bars indicate the product yield. Reactions contained 20 mM αGlc 1-P and 200 mM acceptor.

NMR data show that aldose sugars give α-configured glycosyl-phosphate products, except D-glucosamine which is phosphorylated at the 6-OH. L-Sorbose is phosphorylated at the 1-OH, D-fructose gives predominantly the 1-phosphate product, even though some 6-phosphate is also synthesized. Sugar alcohols are likely phosphorylated at primary OH, but product identity was not determined in these cases.

Figure 11:
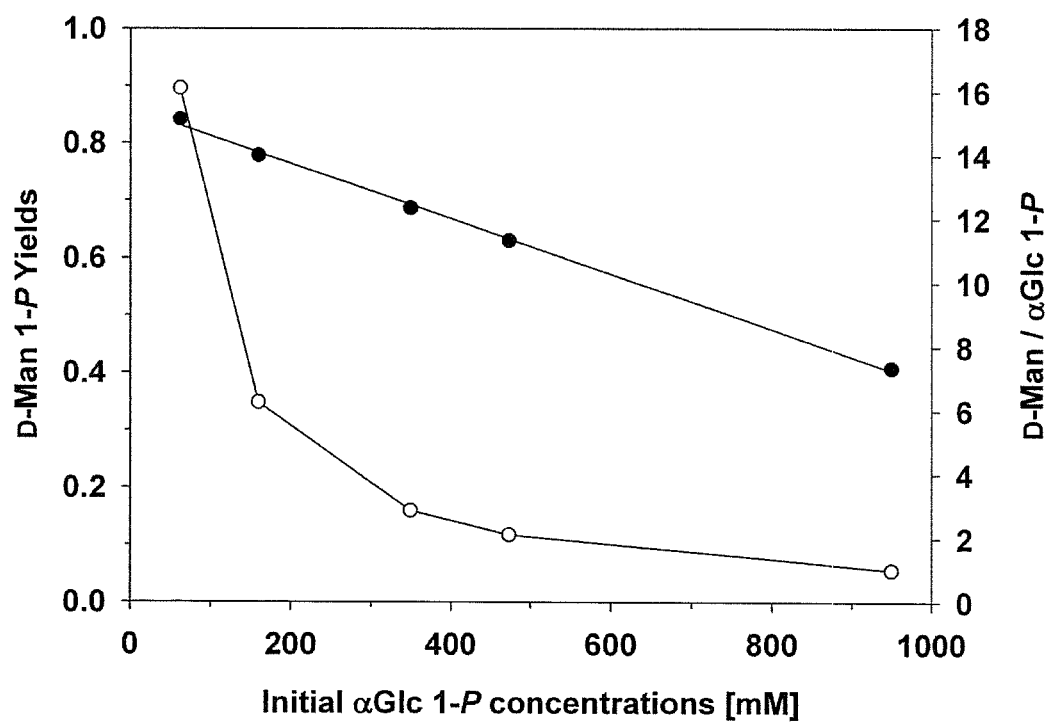
FIG. 11: Dependency of D-mannose 1-P yield on the acceptor to donor ratio. In independent reaction set-ups, the D-glucose 1-phosphate concentration (50 mM, 160 mM, 400 mM, 500 mM and 1M) and the glucose-1-phosphatase concentration (0.3 μM, 1.3 μM, 1.7 μM and 3.3 μM) were varied, while the D-mannose (1 M) concentration remained constant. Symbols indicate: (●) D-mannose 1-phosphate yield and (○) acceptor to donor ratio (D-Man/αGlc 1-P).

FIG. 11 shows the dependency of D-mannose 1-P yield on the acceptor to donor ratio. In independent reaction set-ups, the D-glucose 1-phosphate concentration (50 mM, 160 mM, 400 mM, 500 mM and 1M) and the glucose-1-phosphatase concentration (0.3 μM, 1.3 μM, 1.7 μM and 3.3 μM) were varied, while the D-mannose (1 M) concentration remained constant. Concentrations of about 200-400 mM phosphorylated product (here: α-Man 1-P) can be obtained. Yields are good (≥50%), and there is no need to use large excess of acceptor substrate.

Figure 12:
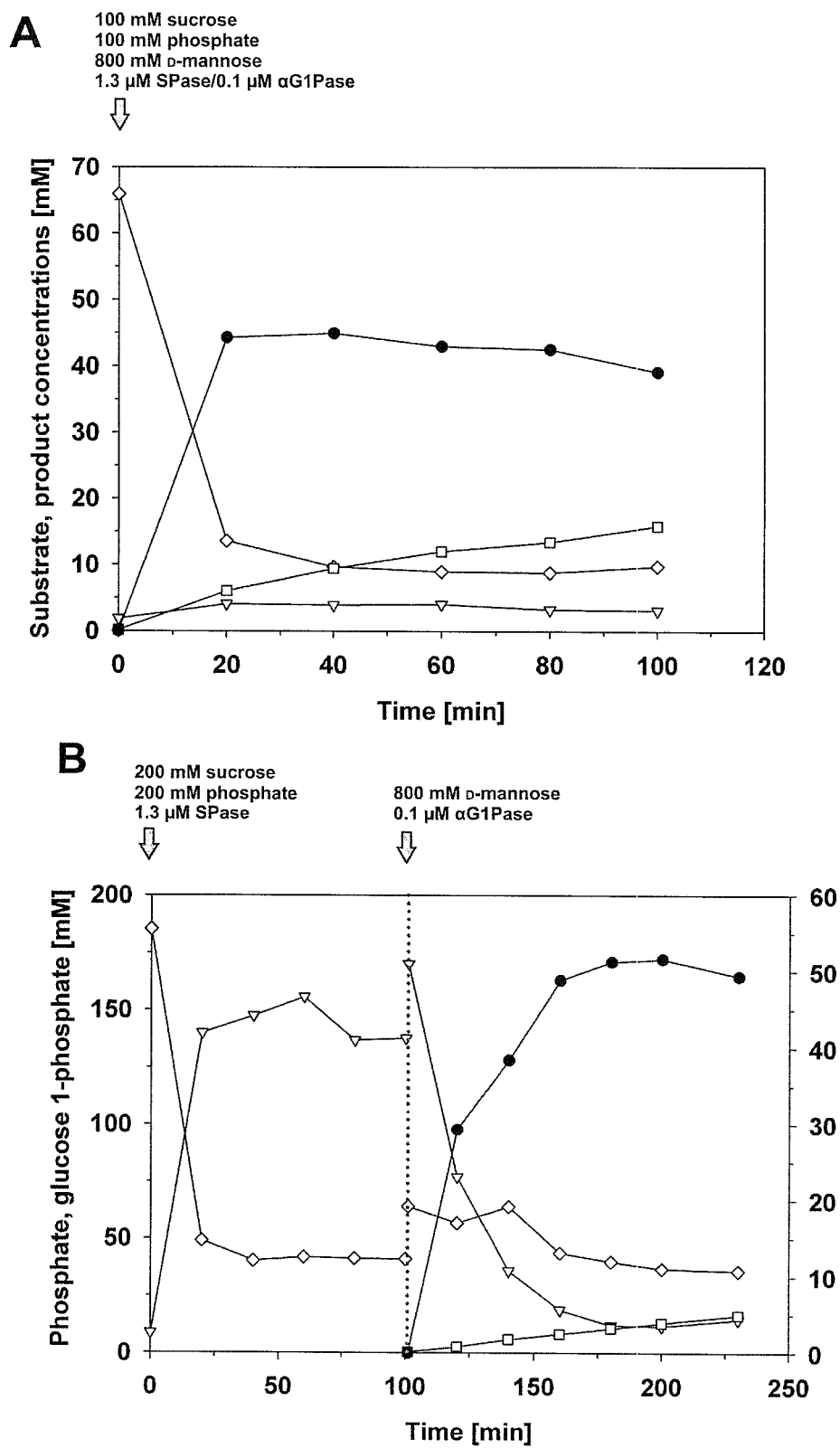
FIG. 12: (A) One-pot, two-step cascade reaction operated in simultaneous reaction mode. Substrates (100 mM sucrose, 100 mM phosphate*, 800 mM D-mannose) and enzymes (1.3 μM SPase, 0.1 μM αG1Pase) are added simultaneously in the beginning. (B) One-pot, two-step cascade reaction operated in sequential mode. In the first step, sucrose and phosphate (200 mM each) is converted to D-glucose 1-phosphate and D-fructose catalysed by SPase (1.3 μM SPase). In the second step, αG1Pase (0.1 μM) converts D-glucose 1-phosphate and D-mannose (final concentration: 800 mM) to D-mannose 1-phosphate and by-products. Reaction conditions: 50 mM MES, pH 7.0, 37° C., 650 rpm. Symbols indicate: D-glucose 1-phosphate (▽), D-glucose 6-phosphate (○), D-mannose 1-phosphate (●) and phosphate (◇).

One-pot, two-step cascade reaction operated in simultaneous reaction mode and One-pot, two-step cascade reaction operated in sequential mode were performed. For the One-pot, two-step reactions operated in simultaneous mode, substrates (100 mM sucrose, 100 mM phosphate*, 800 mM D-mannose) and enzymes (1.3 μM SPase, 0.1 μM αG1Pase) are added simultaneous in the beginning. In sequential mode, in the first step, sucrose and phosphate (200 mM each) is converted to D-glucose 1-phosphate and D-fructose catalysed by SPase (1.3 μM SPase) and in the second step, αG1Pase (0.1 μM) converts D-glucose 1-phosphate and D-mannose (final concentration: 800 mM) to D-mannose 1-phosphate and by-products. The results are shown in FIG. 12.

REFERENCES

1. Dzeja P P, Terzic A. 2003. Phosphotransfer networks and cellular energetics. J. Exp. Biol. 206:2039-2047.
2. Berg J M, Tymoczko J L, Stryer L. 2002. Biochemistry, 5th ed. W H Freeman, New York, USA.
3. Wunschiers R. 2012. Carbohydrate metabolism and citrate cycle, p. 37-58. In Biochemical Pathways: An Atlas of Biochemistry and Molecular Biology, 2nd ed. John Wiley & Sons, Inc., Hoboken, USA.
4. Knowles J R. 1980. Enzyme-catalyzed phosphoryl transfer reactions. Annu. Rev. Biochem. 49:877-919.
5. Lassila J K, Zalatan J G, Herschlag D. 2011. Biological phosphoryl-transfer reactions: understanding mechanism and catalysis. Annu. Rev. Biochem. 80:669-702.
6. Frey P A, Hedgeman A D. Phosphotransfer and nucleotidyltransfer, p. 476-546. In Enzymatic reaction mechanisms. Oxford University Press, Oxford, IJK.
7. Allen K N, Dunaway-Mariano D. 2004. Phosphoryl group transfer: evolution of a catalytic scaffold. Trends Biochem. Sci. 29:495-503.
8. Granot D, Kelly G, Stein O, David-Schwartz R. 2014. Substantial roles of hexokinase and fructokinase in the effects of sugars on plant physiology and development. J. Exp. Bot. 65:809-819.
9. Agius L. 2008. Glucokinase and molecular aspects of liver glycogen metabolism. Biochem. J. 414:1-18.

10. Kawai S, Mukai T, Mori S, Mikami B, Murata K. 2005. Hypothesis: structures, evolution, and ancestor of glucose kinases in the hexokinase family. J. Biosci. Bioeng. 99:320-330.
11. Wilson J E. 2003. Isozymes of mammalian hexokinase: structure, subcellular localization and metabolic function. J. Exp. Biol. 206:2049-2057.
12. Kornberg H L. 2001. Routes for fructose utilization by *Escherichia coli*. J. Mol. Microbiol. Biotechnol. 3:355-359.
13. Luley-Goedl C, Nidetzky B. 2010. Carbohydrate synthesis by disaccharide phosphorylases: reactions, catalytic mechanisms and application in the glycosciences. Biotechnol. J. 5:1324-1338.
14. Nakai H, Kitaoka M, Svensson B, Ohtsubo K. 2013. Recent development of phosphorylases possessing large potential for oligosaccharide synthesis. Curr. Opin. Chem. Biol. 17:301-309.
15. Westheimer F H. 1987. Why nature chose phosphates. Science 235:1173-1178.
16. Kamerlin S C L, Sharma P K, Prasad R B, Warshel A. 2013. Why nature really chose phosphate. Q. Rev. Biophys. 46:1-132.
17. Morrow J R, Amyes T L, Richard J P. 2008. Phosphate binding energy and catalysis by small and large molecules. Acc. Chem. Res. 41:539-548.
18. Nagano N, Orengo C A, Thornton J M. 2002. One fold with many functions: the evolutionary relationships between TIM barrel families based on their sequences, structures and functions. J. Mol. Biol. 321:741-765.
19. Klimacek M, Krahulec S, Sauer U, Nidetzky B. 2010. Limitations in xylose-fermenting *Saccharomyces cerevisiae*, made evident through comprehensive metabolite profiling and thermodynamic analysis. Appl. Environ. Microbiol. 76:7566-7574.
20. Zhang G-F, Sadhukhan S, Tochtrop G P, Brunengraber H. 2011. Metabolomics, pathway regulation, and pathway discovery. J. Biol. Chem. 286:23631-23635.
21. Büscher J M, Czernik D, Ewald J C, Sauer U, Zamboni N. 2009. Cross-platform comparison of methods for quantitative metabolomics of primary metabolism. Anal. Chem. 81:2135-2143.
22. McCloskey D, Palsson BØ, Feist A M. 2013. Basic and applied uses of genome-scale metabolic network reconstructions of *Escherichia coli*. Mol. Syst. Biol. 9:661.
23. Auriol D, Lefevre F, Nalin R, Redziniak G. April 2011. Cosmetic and pharmaceutical composition comprising N-acetylglucosamine-6-phosphate. US 20130012475.
24. Auriol D, Nalin R, Lefevre F, Ginolhac A, Guembecker D D, Zago C. November 2008. Method for preparing C-6 phosphorylated D-aldohexoses and C-6 phosphorylated D-aldohexose derivatives. EP 2150620.
25. Shin W-J, Kim B-Y, Bang W-G. 2007. Optimization of ascorbic acid-2-phosphate production from ascorbic acid using resting cell of *Brevundimonas diminuta*. J. Microbiol. Biotechnol. 17:769-773.
26. Goedl C, Schwarz A, Minani A, Nidetzky B. 2007. Recombinant sucrose phosphorylase from *Leuconostoc mesenteroides*: characterization, kinetic studies of transglucosylation, and application of immobilised enzyme for production of α-D-glucose 1-phosphate. J. Biotechnol. 129:77-86.
27. Van der Borght J, Desmet T, Soetaert W. 2010. Enzymatic production of β-D-glucose-1-phosphate from trehalose. J. Biotechnol. 5:986-993.
28. De Groeve M R M, De Baere M, Hoflack L, Desmet T, Vandamme E J, Soetaert W. 2009. Creating lactose phosphorylase enzymes by directed evolution of cellobiose phosphorylase. Protein Eng. Des. Sel. 22:393-399.
29. Lange C F, Kohn P. 1961. Substrate specificity of hexokinases. J. Biol. Chem. 236:1-5.
30. Nishimasu H, Fushinobu S, Shoun H, Wakagi T. 2006. Identification and characterization of an ATP-dependent hexokinase with broad substrate specificity from the hyperthermophilic archaeon *Sulfolobus tokodaii*. J. Bacteriol. 188:2014-2019.
31. Nishimoto M, Kitaoka M. 2007. Identification of N-acetylhexosamine 1-kinase in the complete lacto-N-biose I/galacto-N-biose metabolic pathway in *Bifidobacterium longum*. Appl. Environ. Microbiol. 73:6444-6449.
32. Cai L, Guan W, Kitaoka M, Shen J, Xia C, Chen W, Wang P G. 2009. A chemoenzymatic route to N-acetylglucosamine-1-phosphate analogues: substrate specificity investigations of N-acetylhexosamine 1-kinase. Chem. Commun. 2944-2946.
33. Chen M, Chen L, Zou Y, Xue M, Liang M, Jin L, Guan W, Shen J, Wang W, Wang L, Liu J, Wang P G. 2011. Wide sugar substrate specificity of galactokinase from *Streptococcus pneumoniae* TIGR4. Carbohydr. Res. 346:2421-2425.
34. Zhao H, van der Donk W A. 2003. Regeneration of cofactors for use in biocatalysis, Curr. Opin. Biotechnol. 14:583-589.
35. Berke W, Schüz H J, Wandrey C, Morr M, Denda G, Kula M R. 1988. Continuous regeneration of ATP in enzyme membrane reactor for enzymatic syntheses. Biotechnol. Bioeng. 32:130-139.
36. Wilson I B, Dayan J, Cyr K. 1964. Some properties of alkaline phosphatase from *Escherichia coli*: transphosphorylation. J. Biol. Chem. 239:4182-4185.
37. Van Herk T, Hartog A F, van der Burg A M, Wever R. 2005. Regioselective phosphorylation of carbohydrates and various alcohols by bacterial acid phosphatases; probing the substrate specificity of the enzyme from *Shigella flexneri*. Adv. Synth. Catal. 347:1155-1162.
38. Babich L, Hartog A F, van der Horst M A, Wever R. 2012. Continuous-flow reactor-based enzymatic synthesis of phosphorylated compounds on a large scale. Eur. J. Chem. 18:6604-6609.
39. Babich L, Hartog A F, van Hemert L J, Rutjes F P, Wever R. 2012. Synthesis of carbohydrates in a continuous flow reactor by immobilized phosphatase and aldolase. ChemSusChem 5:2348-53.
40. Fernley H N, Walker P G. 1967. Studies on alkaline phosphatase-inhibition by phosphate derivatives and substrate specificity. Biochem. J. 104:1011-1018.
41. O'Brien P J, Herschlag D. 2002. Alkaline phosphatase revisited: hydrolysis of alkyl phosphates. Biochemistry 41:3207-3225.
42. Goedl C, Sawangwan T, Wildberger P, Nidetzky B. 2010. Sucrose phosphorylase: a powerful transglucosylation catalyst for synthesis of α-D-glucosides as industrial fine chemicals. Biocatal. Biotransformation 28:10-21.
43. Renirie R, Pukin A, van Lagen B, Franssen M C R. 2010. Regio- and stereoselective glucosylation of diols by sucrose phosphorylase using sucrose or glucose 1-phosphate as glucosyl donor. J. Mol. Catal. B Enzym. 67:219-224.
44. Pradel E, Marck C, Boquet P L. 1990. Nucleotide sequence and transcriptional analysis of the *Escherichia coli* agp gene encoding periplasmic acid glucose-1-phosphatase. J. Bacteriol. 172:802-807.

45. Lee D C, Cottrill M A, Forsberg C W, Jia Z. 2003. Functional insights revealed by the crystal structures of *Escherichia coli* glucose-1-phosphatase. J. Biol. Chem. 278:31412-31418.
46. Kuznetsova E, Proudfoot M, Gonzalez C F, Brown G, Omeichenko M V, Borozan I, Carmel L, Wolf Y I, Mori H, Savchenko A V, Arrowsmith C H, Koonin E V, Edwards A M, Yakunin A F. 2006. Genome-wide analysis of substrate specificities of the *Escherichia coli* haloacid dehalogenase-like phosphatase family. J. Biol. Chem. 281:36149-36161.
47. Burroughs A M, Allen K N, Dunaway-Mariano D, Aravind L. 2006. Evolutionary genomics of the HAD superfamily: understanding the structural adaptations and catalytic diversity in a superfamily of phosphoesterases and allied enzymes. J. Mol. Biol. 361:1003-1034.
48. Collet J F, Stroobant V, Pirard M, Delpierre G, Van Schaftingen I E. 1998. A new class of phosphotransferases phosphorylated on an aspartate residue in an amino-terminal DXDX(T/V) motif. J. Biol. Chem. 273:14107-14112.
49. Lahiri S D, Zhang G, Dunaway-Mariano D, Allen K N. 2006. Diversification of function in the haloacid dehalogenase enzyme superfamily: The role of the cap domain in hydrolytic phosphoruscarbon bond cleavage. Bioorganic Chem. 34:394-409.
50. Morals M C, Zhang W, Baker A S, Zhang G, Dunaway-Mariano D, Allen K N. 2000. The crystal structure of *Bacillus cereus* phosphonoacetaldehyde hydrolase: insight into catalysis of phosphorus bond cleavage and catalytic diversification within the HAD enzyme superfamily. Biochemistry 39:10385-10396.
51. Wildberger P, Todea A, Nidetzky B. 2012. Probing enzyme-substrate interactions at the catalytic subsite of *Leuconostoc mesenteroides* sucrose phosphorylase with site-directed mutagenesis: the roles of Asp49 and Arg395. Biocatal Biotransformation 30:326-337.
52. Krahulec S, Armao G C, Weber H, Klimacek M, Nidetzky B. 2008. Characterization of recombinant *Aspergillus fumigatus* mannitol-1-phosphate 5-dehydrogenase and its application for the stereoselective synthesis of protio and deuterio forms of D-mannitol 1-phosphate. Carbohydr. Res. 343:1414-1423.
53. Gibson D G, Young L, Chuang R Y, Venter J C, Hutchison C A, Smith H O. 2009. Enzymatic assembly of DNA molecules up to several hundred kilobases. Nat. Methods 6:343-345.
54. Whitmore L, Wallace B A. 2008. Protein secondary structure analyses from circular dichroism spectroscopy: methods and reference databases. Biopolymers 89:392-400.
55. Shevchenko A, Wilm M, Vorm O, Mann M. 1996. Mass spectrometric sequencing of proteins silver-stained polyacrylamide gels. Anal. Chem. 68:850-858.
56. Saheki S, Takeda A, Shimazu T. 1985. Assay of inorganic phosphate in the mild pH range, suitable for measurement of glycogen phosphorylase activity. Anal. Biochem. 148:277-281.
57. Eis C, Nidetzky B. 1999. Characterization of trehalose phosphorylase from *Schizophyllum commune*. Biochem. J. 341:385-393.
58. Bradford M M. 1976. A rapid and sensitive method for the quantitation of microgram quantities of protein utilizing the principle of protein-dye binding. Anal. Biochem. 72:248-254.
59. Jia Z, Cottrill M, Pal G P, Lee D, Sung M, Forsberg C W, Phillips J P. 2001. Purification, crystallization and preliminary X-ray analysis of the *Escherichia coli* glucose-1-phosphatase. Acta Crystallogr. Sect. D 57:314-316.
60. Cottrill M A, Golovan S P, Phillips J P, Forsberg C W. 2002. Inositol phosphatase activity of the *Escherichia coli* agp-encoded acid glucose-1-phosphatase. Can. J. Microbiol. 48:801-809.
61. Kietzmann M, Schwab H, Pichler H, Ivancic M, May O, Luiten R G M. July 2011. Preparation of an esterase. WO 2009004093.
62. Graff G, Krick T P, Walseth T F, Goldberg N D. 1980. The use of [$^{18}O_4$]phosphoric acid in the quantitation of phosphate by gas-liquid chromatography-mass spectrometry analysis. Anal. Biochem. 107:324-331.
63. Pradines A, Klaebe A, Perie J, Paul F, Monsan P. 1991. Large-scale enzymatic synthesis of glycerol 1-phosphate. Enzyme Microb. Technol. 13:19-23.
64. Oh B-C, Choi W-C, Park S, Kim Y-., Oh T-K. 2004. Biochemical properties and substrate specificities of alkaline and histidine acid phytases. Appl. Microbiol. Biotechnol. 63:362-372.
65. Ray W J Jr, Roscelli G A. 1964. A kinetic stuy of the phosphoglucomutase pathway. J. Biol. Chem. 239:1228-1236.
66. Mitchell D B, Vogel K, Weimann B J, Pasamontes L, van Loon APGM. 1997. The phytase subfamily of histidine acid phosphatases: isolation of genes for two novel phytases from the fungi *Aspergillus terreus* and *Mycelio-phthora thermophila*. Microbiology 143:245-252.
67. Tomschy A, Brugger R, Lehmann M, Svendsen A, Vogel K, Kostrewa D, Lassen S F, Burger D, Kronenberger A, van Loon APGM, Pasamontes L, Wyss M. 2002. Engineering of phytase for improved activity at low pH. Appl. Environ. Microbiol. 68:1907-1913.
68. Pogell B M. 1953. A new synthesis of fructose-1-phosphate with phosphorus pentoxide. J. Biol. Chem. 201:645-649.
69. Fessner W-D, Sinerius G, Schneider A, Dreyer M, Schulz G E, Badia J, Aguilar J. 1991. Diastereoselective enzymatic aldol additions: L-rhamnulose and L-fuculose 1-phosphate aldolases from *E. coli*. Angew. Chem. Int. Ed, Engl. 30:555-558.
70. Lefebvre M J, Gonzalez N S, Pontis H G. 1964. Anion-exchange chromatography of sugar phosphates with triethylammonium borate. J. Chromatogr. 15:495-500.
71. Smits H P, Cohen A, Buttler T, Nielsen J, Olsson L. 1998. Cleanup and analysis of sugar phosphates in biological extracts by using solid-phase extraction and ani-on-exchange chromatography with pulsed amperometric detection. Anal. Biochem. 261:36-42.
72. Lu Z, Dunaway-Mariano D, Allen K N. 2005. HAD superfamily phosphotransferase substrate diversification: structure and function analysis of HAD subclass IIB sugar phosphatase BT4131. Biochemistry 44:8684-8696.
73. Tanaka N, Hasan Z, Hartog A F, van Herk T, Wever R, Sanders R J. 2003. Phosphorylation and dephosphorylation of polyhydroxy compounds by class A bacterial acid phosphatases. Org. Biomol. Chem. 1:2833-2839.
74. Mihara Y, Utagawa T, Yamada H, Asano Y. 2001. Acid phosphatase/phosphotransferases from enteric bacteria. J. Biosci. Bioeng. 92:50-54.
75. Koerner TAW, Voll R J, Cary L W, Younathan E S. 1980. Carbon-13 nuclear magnetic resonance studies and anomeric composition of ketohexose phosphates in solution. Biochemistry 19:2795-2801.
76. Lu Z, Dunaway-Mariano D, Allen K N. 2008. The catalytic scaffold of the haloalkanoic acid dehalogenase enzyme superfamily acts as a mold for the trigonal bipyramidal transition state. Proc. Natl. Acad. Sci. 105: 5687-5692.

The invention claimed is:

1. A method of producing one or more sugar-1-phosphates by enzymatic transphosphorylation comprising:
   (i) providing one or more sugar substrates selected from the group consisting of aldoses and ketoses,
   (ii) providing one or more phosphate donor substrates selected from the group consisting of phosphorylated carbohydrates,
   (iii) providing an alpha-glucose-1-phosphatase or an enzyme having alpha-glucose-1-phosphatase activity,
   (iv) incubating the one or more sugar substrates provided in step (i) and the one or more phosphate donor substrates provided in step (ii) with the alpha-glucose-1-phosphatase or, respectively, the enzyme having alpha-glucose-1-phosphatase activity provided in step (iii) under conditions which allow transphosphorylation to obtain one or more sugar-1-phosphates,
   (v) optionally, purifying the one or more sugar-1-phosphates obtained in step (iv).

2. The method according to claim 1, wherein the one or more sugar substrate is selected from the group consisting of glucose, fructose, galactose, fucose, mannose, sorbose, xylose, arabinose, and rhamnose.

3. The method according to claim 1, wherein the one or more phosphate donor substrate is selected from the group consisting of alpha-glucose-1-phosphate, glucose-6-phosphate, fructose-6-phosphate and fructose-1-phosphate.

4. The method according to claim 1, wherein the phosphate donor substrate or one of the phosphate donor substrates provided in step (ii) is alpha-glucose-1-phosphate.

5. The method according to claim 4 wherein step (ii) comprises an enzymatic conversion of sucrose to D-fructose and alpha-D-glucose-1-phosphate by a sucrose phosphorylase or an enzyme having sucrose phosphorylase activity in the presence of phosphate or one or more sources of phosphate.

6. The method according to claim 5, wherein step (ii) and step (iv) and, optionally, step (iii) are carried out simultaneously.

7. The method according to claim 5, wherein the method is performed in the presence of a biocatalyst, having sucrose phosphorylase activity and alpha-glucose-1-phosphatase activity and/or comprising a sucrose phosphorylase and an alpha-glucose-1-phosphatase.

8. The method according to claim 1, wherein step (iii) comprises the expression of an alpha-glucose-1-phosphatase or an enzyme having alpha-glucose-1-phosphatase activity by a host cell.

9. The method according to claim 8, wherein the alpha-glucose-1-phosphatase or the enzyme having alpha-glucose-1-phosphatase activity, respectively, is expressed as a recombinant fusion protein comprising a tag suitable for isolation of the alpha-glucose-1-phosphatase or the enzyme having alpha-glucose-1-phosphatase activity.

* * * * *